US010380399B2

(12) United States Patent
Call et al.

(10) Patent No.: US 10,380,399 B2
(45) Date of Patent: Aug. 13, 2019

(54) ULTRASOUND IMAGING SYSTEMS AND METHODS FOR DETECTING OBJECT MOTION

(71) Applicant: MAUI IMAGING, INC., San Jose, CA (US)

(72) Inventors: Josef R. Call, Campbell, CA (US); Henry A. Davis, Ash Fork, AZ (US); Donald F. Specht, Los Altos, CA (US)

(73) Assignee: MAUI IMAGING, INC., San Jose, CA (US)

( * ) Notice: Subject to any disclaimer, the term of this patent is extended or adjusted under 35 U.S.C. 154(b) by 0 days.

(21) Appl. No.: 15/558,452

(22) PCT Filed: Mar. 30, 2016

(86) PCT No.: PCT/US2016/024999
§ 371 (c)(1),
(2) Date: Sep. 14, 2017

(87) PCT Pub. No.: WO2016/160981
PCT Pub. Date: Oct. 6, 2016

(65) Prior Publication Data
US 2018/0068155 A1     Mar. 8, 2018

Related U.S. Application Data

(60) Provisional application No. 62/140,296, filed on Mar. 30, 2015, provisional application No. 62/235,411, filed on Sep. 30, 2015.

(51) Int. Cl.
*G06K 9/00*     (2006.01)
*A61B 8/06*     (2006.01)
*A61B 8/08*     (2006.01)
*G01S 15/89*     (2006.01)
*G01S 7/52*     (2006.01)

(52) U.S. Cl.
CPC .............. *G06K 9/0002* (2013.01); *A61B 8/06* (2013.01); *A61B 8/485* (2013.01); *G01S 7/52042* (2013.01); *G01S 15/8915* (2013.01); *G01S 15/8918* (2013.01); *G01S 15/8927* (2013.01); *G01S 15/8993* (2013.01)

(58) Field of Classification Search
None
See application file for complete search history.

(56) References Cited

U.S. PATENT DOCUMENTS

| | | | |
|---|---|---|---|
| 2012/0057428 A1* | 3/2012 | Specht | A61B 8/00 367/13 |
| 2013/0070062 A1* | 3/2013 | Fouras | A61B 6/486 348/50 |
| 2014/0043933 A1* | 2/2014 | Belevich | A61B 8/587 367/11 |
| 2014/0058266 A1* | 2/2014 | Call | A61B 8/14 600/448 |
| 2014/0147013 A1* | 5/2014 | Shandas | A61B 8/481 382/107 |
| 2017/0119352 A1* | 5/2017 | Anand | A61B 8/0866 |

\* cited by examiner

*Primary Examiner* — Delomia L Gilliard
(74) *Attorney, Agent, or Firm* — Shay Glenn LLP

(57) ABSTRACT

Ping-based imaging systems may be used for tracking motion of hard or soft objects within an imaged medium. Motion detection and motion tracking may be performed by defining fingerprint points and tracking the position of each fingerprint point based on the echoes of multiple transmitted pings.

16 Claims, 5 Drawing Sheets

ULTRASOUND IMAGING SYSTEMS AND METHODS FOR DETECTING OBJECT MOTION

CROSS-REFERENCE TO RELATED APPLICATIONS

This application claims the benefit of U.S. Provisional Patent Application No. 62/140,296, filed on Mar. 30, 2015, titled "Ultrasound Imaging Systems and Methods for Detecting Object Motion", and U.S. Provisional Patent Application No. 62/235,411, filed on Sep. 30, 2015, titled "Ultrasound Imaging Systems and Methods for Detecting Object Motion", the contents of which are incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

FIELD

This application relates generally to the field of ultrasound imaging, and more particularly to high speed motion tracking using ping-based ultrasound imaging.

BACKGROUND

In conventional scanline-based ultrasonic imaging, a focused beam of ultrasound energy is transmitted into body tissues to be examined and echoes returned along the same line are detected and plotted to form a portion of an image along the scanline. A complete image may be formed by repeating the process and combining image portions along a series of scanlines within a scan plane. Any information in between successive scanlines must be estimated by interpolation.

The same process has been extended to obtaining ultrasonic images of three-dimensional volumes by combining images from multiple adjacent slices (where each slice is in a different scan plane). Again, any information from any space in between successive scan planes must be estimated by interpolation. Because time elapses between capturing complete 2D slices, obtaining 3D image data for a moving object may be significantly impaired. So-called "4D" imaging systems (in which the fourth dimension is time) strive to produce moving images (i.e., video) of 3D volumetric space. Scanline-based imaging systems also have an inherent frame-rate limitation which creates difficulties when attempting 4D imaging on a moving object.

As a result of these and other factors, some of the limitations of existing 2D and 3D ultrasonic imaging systems and methods include poor temporal and spatial resolution, imaging depth, speckle noise, poor lateral resolution, obscured tissues and other such problems.

Significant improvements have been made in the field of ultrasound imaging with the creation of multiple aperture imaging, examples of which are shown and described in Applicant's prior patents and applications. Multiple aperture imaging methods and systems allow for substantially increased imaging resolution and substantially higher frame rates than conventional ultrasound imaging systems.

SUMMARY

A method of tracking motion of an object with an imaging system is provided comprising the steps of defining a plurality of fiducial regions in a region of interest with a controller of the imaging system, defining a fingerprint point within each fiducial region with the controller, wherein the fingerprint represents an area smaller than any detail resolvable by the imaging system, transmitting a series of unfocused ultrasound pings into the region of interest from a transducer array of the imaging system, receiving echoes from the series of transmitted unfocused ultrasound pings with a plurality of transducer elements of the transducer array, storing echo data received by each of the plurality of transducer elements in a separate memory string, detecting movement of at least one fingerprint point with the controller, and communicating a signal with the controller indicating that movement of the object relative to the transducer array has occurred.

In some embodiments, the method further comprises obtaining at least one image of the region of interest with the imaging system, and wherein defining the plurality of fiducial regions comprises selecting a plurality of points in the at least one image.

In some embodiments, obtaining at least one image of a region of interest comprises obtaining at least two images containing at least a portion of the object, the at least two images lying in intersecting two-dimensional planes that also intersect the object, wherein defining the fingerprint point comprises defining a first fingerprint point at an intersection between the two-dimensional planes and the object, defining a second fingerprint point in a first of the at least two images, and defining a third fingerprint point in a second image not at the intersection.

In other embodiments, detecting movement of the at least one fingerprint point comprises identifying a fingerprint point in each memory string, and detecting a shift in a position of the fingerprint point in each memory string.

In one embodiment, the at least one fingerprint point comprises at least one machine-identifiable peak.

In other embodiments, the method further comprises combining memory strings from two or more unfocused ultrasound pings to form a combined memory string before detecting a shift in a position of a first one of the fingerprint points in the combined memory string.

In one embodiment, the method further comprises combining memory strings from two or more transducer elements of the transducer array to form a combined memory string before detecting a shift in a position of a first one of the fingerprint points in the combined memory string.

In some embodiments, detecting movement of the at least one fingerprint point comprises identifying a fingerprint pattern with the controller in a location other than an original location.

In another embodiment, the method further comprises tracking motion of the object with the controller, comprising obtaining a pre-movement fingerprint pattern with the controller corresponding to each fingerprint point contained within each fiducial region, defining a search region surrounding each fingerprint point with the controller, obtaining a plurality of post-movement search images with the controller by retrieving post-movement data corresponding to the search regions surrounding each of the fingerprint points and beamforming the search regions, searching each post-movement search region with the controller for a new position of a corresponding one of the pre-movement fingerprint patterns, determining a new position for at least one of the fingerprint points with the controller based on finding a fingerprint pattern in a search region, and communicating a signal with the controller indicating a new position of the at least one fingerprint point or a new position of the object.

In one embodiment, only the search regions are beamformed and echo data that does not correspond to one of the search regions is not beamformed during the step of tracking motion of the object.

In some embodiments, the method further comprises detecting a shift in a position of a first one of the fingerprint points based on data in a plurality of the memory strings corresponding to a plurality of receiving transducer elements.

In another embodiment, the plurality of transducer elements are closer to opposite ends of the transducer array from one another than they are to one another.

In some embodiments, each of the fingerprint points has an area of between 1 square nanometer and 100 square micrometers.

In other embodiments, each of the defined fingerprints represents an area with a maximum dimension that is less than half of a size of a smallest detail resolvable by an imaging system performing the method.

In additional embodiments, each of the defined fingerprints represents an area with a maximum dimension that is less than half of a wavelength of the ultrasound pings transmitted from the array.

In some embodiments, each of the defined fingerprints represents an area with a maximum dimension that is less than a quarter of a wavelength of the ultrasound pings transmitted from the array.

In another embodiment, each of the defined fingerprints represents an area with a maximum dimension that is less than a tenth of a wavelength of the ultrasound pings transmitted from the array.

In one embodiment, all of the fiducial regions lie within a free depth range defined as a range of distance from each transducer element in which returning echoes result from only a single transmitted ping, and transmitting pings at a rate greater than an inverse of a maximum round-trip travel time between a transmitting transducer element, a furthest reflector, and a receive element furthest from the transmitting element.

In another embodiment, the transducer array comprises a first plurality of one-dimensional linear transducer elements aligned with a first image plane and a second plurality of one-dimensional linear transducer elements aligned with a second image plane that intersects the first image plane, and wherein transmitting a series of unfocused pings into the region of interest comprises transmitting a first series of pings from a first single element of the first plurality of one-dimensional transducer elements and transmitting a second series of pings from a second single element of the second plurality of one-dimensional transducer elements.

In some embodiments, the transducer array comprises a first plurality of one-dimensional linear transducer elements aligned with a first image plane extending into the region of interest, a second plurality of one-dimensional linear transducer elements aligned with a second image plane extending into the region of interest, the second image plane intersecting the first image plane, and a point source transmitter element; and wherein transmitting a series of unfocused pings into the region of interest comprises transmitting a series of unfocused pings from the point source transmitter element.

In another embodiment, the point source transmitter element is positioned at an intersection of the first image plane and the second image plane.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
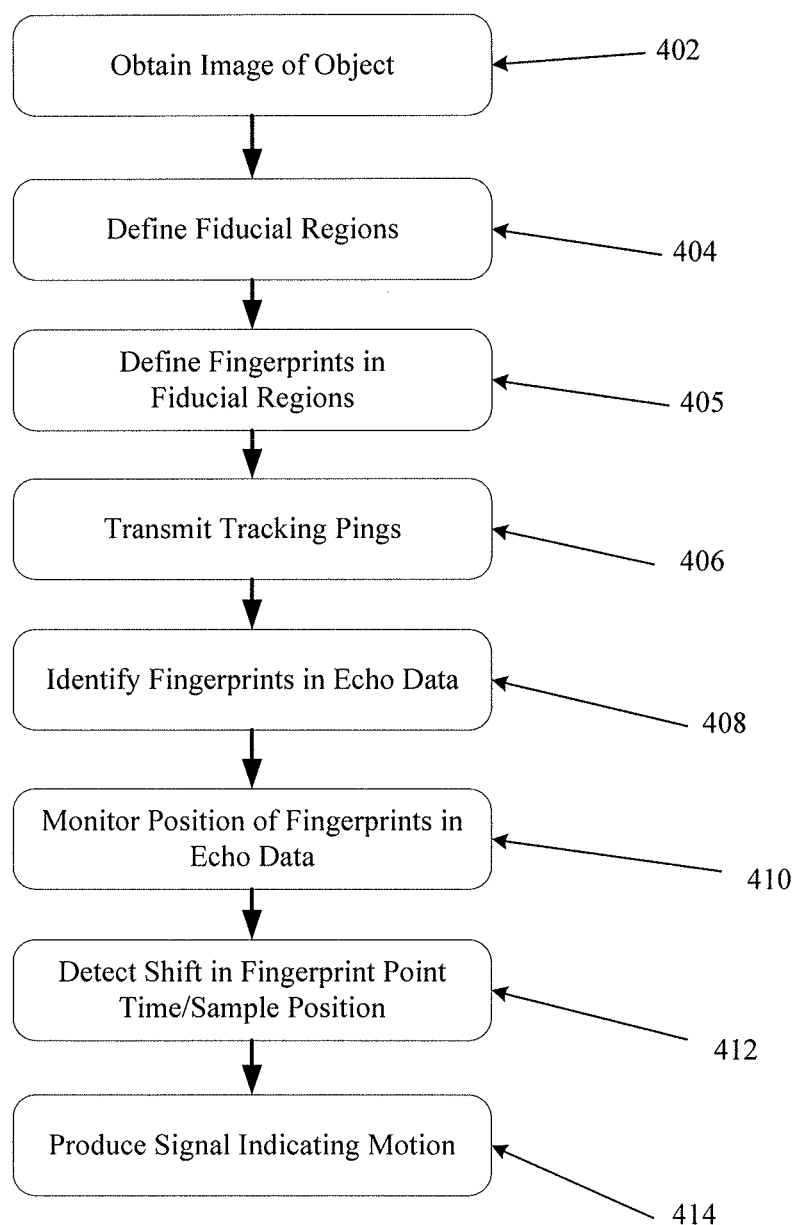
FIG. 1 is a process flow diagram illustrating a process for detecting motion in an object using an ultrasound system.

The various embodiments will be described in detail with reference to the accompanying drawings. References made to particular examples and implementations are for illustrative purposes, and are not intended to limit the scope of the invention or the claims.

The present disclosure provides systems and methods for using high speed ultrasound techniques for detecting motion of objects, tissues, or substances within an imaged medium. Embodiments of ultrasound motion detection systems and methods described herein may provide various advantages that cannot be met by other available systems. Such advantages may include potential motion detection frame rates of up to 10,000 frames/second, motion detection latencies of under 10 ms, and the ability to detect and track motion with precision on a scale far less than a wavelength of ultrasound used. Techniques described herein may be used to detect and track motion of points smaller than any resolvable object in the ultrasound imaging system being used.

For example, systems and methods herein may be used to detect and track movement of an object by less than 0.05 mm, with less than 1 millisecond of reporting latency, at update rates of more than 10 kHz. Position and velocity of moving objects may be tracked in six degrees of freedom (e.g., linear movement in X, Y, Z directions and rotation about pitch, roll, and yaw axes). In some cases, systems and methods described herein can perform even better than these measures.

The Rayleigh criterion is the generally accepted criterion for determining the size of a minimum resolvable detail (in terms of lateral resolution) achievable by an imaging system. The imaging process is said to be "diffraction-limited" when the first diffraction minimum of the image of one source point coincides with the maximum of another. The Rayleigh criterion, simplified for the case of an ultrasound imaging probe, indicates that the size ('r') of the minimum resolvable detail in lateral resolution of an ultrasound probe with a total aperture of D is r≈1.22λ/D (where λ is the speed-of-ultrasound in the imaged medium divided by ultrasound frequency).

Because there is no transmit beamforming in a ping-based ultrasound imaging system, there is also no axial resolution in the traditional sense attributed to conventional phased array ultrasound. However, the term 'axial resolution' is used in the traditional sense here because it conveys a somewhat similar concept: the ability to distinguish two reflectors lying close together along a radial line originating at a point-source transmitter. The axial resolution of a ping-based ultrasound imaging system is approximately equal to the wavelength (λ) of ultrasound being used (i.e., the speed-of-ultrasound in the imaged medium divided by ultrasound frequency) multiplied by the number of cycles transmitted in each ping.

The various motion detection and motion tracking systems and methods described herein generally utilize an imaging technique referred to herein as "ping-based imaging." This disclosure is organized with a description of ping-based imaging techniques, followed by a description of various motion detection and motion tracking techniques, which in turn is followed by a description of various hardware elements that may be used in combination with the processes and techniques described herein.

Although various embodiments are described herein with reference to ultrasound imaging of various anatomic structures, it will be understood that many of the methods and devices shown and described herein may also be used in other applications, such as imaging and evaluating non-anatomic structures and objects. For example, the various embodiments herein may be applied to non-destructive testing applications such as evaluating the quality, integrity, dimensions, or other characteristics of various structures such as welds, pressure vessels, pipes, structural members, beams, etc. The systems and methods may also be used for imaging and/or testing a range of materials including human or animal tissues, solid metals such as iron, steel, aluminum, or titanium, various alloys or composite materials, etc.

Introduction to Key Terms

The following paragraphs provide useful definitions for some terms used frequently herein. Other terms may also be defined as they are used below.

As used herein the terms "ultrasound transducer" and "transducer" may carry their ordinary meanings as understood by those skilled in the art of ultrasound imaging technologies, and may refer without limitation to any single component capable of converting an electrical signal into an ultrasonic signal and/or vice versa. For example, in some embodiments, an ultrasound transducer may comprise a piezoelectric device. In other embodiments, ultrasound transducers may comprise capacitive micro-machined ultrasound transducers (CMUT), other micro-machined transducers made of electroactive materials such as piezoelectric materials, ferroic materials, ferroelectric materials, pyroelectric materials, electrostrictive materials, or any other transducing material or device capable of converting ultrasound waves to and from electrical signals.

Transducers are often configured in arrays of multiple individual transducer elements. As used herein, the terms "transducer array" or "array" generally refers to a collection of transducer elements attached to a common support structure. An array may typically (though not necessarily) comprise a plurality of transducer elements mounted to a common backing plate or substrate. Such arrays may have one dimension (1D), two dimensions (2D), 1.X dimensions (1.XD) or three dimensions (3D) as those terms are used elsewhere herein and/or as they are commonly understood in the art. Other dimensioned arrays as understood by those skilled in the art may also be used. Annular arrays, such as concentric circular arrays and elliptical arrays may also be used. In some cases, transducer arrays may include irregularly-spaced transducer elements, sparsely positioned transducer elements (also referred to as sparse arrays), randomly spaced transducer elements, or any other geometric or random arrangement of transducer elements. Elements of an array need not be contiguous and may be separated by non-transducing material.

An element of a transducer array may be the smallest discretely functional component of an array. For example, in the case of an array of piezoelectric transducer elements, each element may be a single piezoelectric crystal or a single machined section of a piezoelectric crystal. Alternatively, in an array made up of a plurality of micro-elements (e.g., micro-machined elements, micro-dome elements, or other micro-sized elements), a group of micro-elements may be electrically coupled so as to operate collectively as a single functional element. In such a case, the group of collectively-operating micro-elements As used herein, the terms "transmit element" and "receive element" may carry their ordinary meanings as understood by those skilled in the art of ultrasound imaging technologies. The term "transmit element" may refer without limitation to an ultrasound transducer element which at least momentarily performs a transmit function in which an electrical signal is converted into an ultrasound signal. Transmitted ultrasound signals may be focused in a particular direction, or may be unfocused, transmitting in all directions or a wide range of directions. Similarly, the term "receive element" may refer without limitation to an ultrasound transducer element which at least momentarily performs a receive function in which an ultrasound signal impinging on the element is converted into an electrical signal. Transmission of ultrasound into a medium may also be referred to herein as "insonifying." An object or structure which reflects ultrasound waves may be referred to as a "reflector" or a "scatterer."

As used herein, terms referring to a "position" or "location" of a transducer element refer to an acoustic center position exhibited by the element. In some cases, an acoustic center position of an element may be precisely coincident with a mechanical or geometric center of the element. However, in many cases, an acoustic center position of an element may be different than a mechanical or geometric center of the element due to various factors such as manufacturing irregularities, damage, irregular element geometries, etc. Acoustic center positions of elements may be determined using various calibration techniques such as those described in US Patent Application Publication 2014/0043933, titled "Calibration of Multiple Aperture Ultrasound Probes," and U.S. Pat. No. 9,282,945, titled "Calibration of Ultrasound Probes."

As used herein, the term "aperture" may refer to a single transducer element or a group of transducer elements that are collectively managed as a common group by imaging control electronics. For example, in some embodiments an aperture may be a grouping of elements which may be physically separate and distinct from elements of an adjacent aperture. However, adjacent apertures need not necessarily be physically separate or distinct. Conversely, a single aperture may include elements of two or more physically separate or distinct transducer arrays or elements spaced from one another by any distance or different distances. In some cases, two or more elements need not be adjacent to one another to be included in a common aperture with one another. For example, distinct groups of transducer elements (e.g., a "left aperture") may be constructed from a left array, plus the left half of a physically distinct center array, while a "right aperture" may be constructed from a right array, plus the right half of a physically distinct center array).

As used herein, the terms "receive aperture," "insonifying aperture," and/or "transmit aperture" are used herein to mean an individual element, a group of elements within an array, or even entire arrays, that perform the desired transmit or receive function as a group. In some embodiments, such transmit and receive apertures may be created as physically separate components with dedicated functionality. In other embodiments, any number of send and/or receive apertures may be dynamically defined electronically as needed. In other embodiments, a multiple aperture ultrasound imaging system may use a combination of dedicated-function and dynamic-function apertures. In some cases, elements may be assigned to different apertures during two or more ping cycles (as defined below).

As used herein, the term "ping cycle" refers to a cycle that begins with the transmission of a ping from a transmitter approximating a point source and ends when all available (or all desired) echoes of that transmitted ping have been received by receive transducer elements. In many cases, ping cycles may be distinct and separated by some time period. In other cases, ping cycles may overlap one another in time. That is, an N+1th ping cycle may begin (with transmission of a ping) before an Nth ping cycle is completed.

As used herein, the term "total aperture" refers to the overall size of all imaging apertures in a probe. In other words, the term "total aperture" may refer to one or more dimensions defined by a maximum distance between the furthest-most transducer elements of any combination of transmit and/or receive elements used for a particular imaging cycle. Thus, the total aperture may be made up of any number of sub-apertures designated as send or receive apertures for a particular cycle. In the case of a single-aperture imaging arrangement, the total aperture, sub-aperture, transmit aperture, and receive aperture may all have the same dimensions. In the case of a multiple aperture imaging arrangement, the dimensions of the total aperture include the sum of the dimensions of all send and receive apertures plus any space between apertures.

In some embodiments, two apertures may be located adjacent to one another on a continuous array. In other embodiments, two apertures may overlap one another on a continuous array, such that at least one element functions as part of two separate apertures. The location, function, number of elements and physical size of an aperture may be defined dynamically in any manner needed for a particular application.

Elements and arrays described herein may also be multi-function. That is, the designation of transducer elements or arrays as transmitters in one instance does not preclude their immediate re-designation as receivers in the next instance. Moreover, embodiments of control systems herein include the capabilities for making such designations electronically based on user inputs, pre-set scan or resolution criteria, or other automatically determined criteria.

As used herein, the "image-able field" of the imaging system may be any area or volume of an imaged object or substance that may practically be imaged by the imaging system. For a ping-based imaging system as described herein, the term "image-able field" may be synonymous with the term "insonified region." The term "region of interest" may refer to a two-dimensional or three-dimensional region within the image-able field. The extents of an image-able field relative to a probe may be imposed by physical limits (e.g., based on signal-to-noise ratios or attenuation rates) or may be chosen logical limits (e.g., based on a desired region of interest).

As used herein, the term "pixel" refers to a region of two-dimensional space within an image-able field of the imaging system. The term "pixel" is not intended to be limited to a pixel of a display device, and may represent a region of a real-world-scale object that is either larger or smaller than a display pixel. A "pixel" may represent a region of the image-able field of any real-world size, and in some cases may represent a region smaller than any resolvable object of the imaging system. Pixels may be, but need not necessarily be square or rectangular, and may have any shape allowing for contiguous two-dimensional representation of the image-able field. In some cases, data representing a pixel may not be displayed, but may still be processed as a unit and referred to as a "pixel."

As used herein, the term "voxel" refers to a region of three-dimensional space within an image-able field of the imaging system. The term "voxel" is not intended to be limited to any particular portion of a two-dimensional or three-dimensional display device, and may represent a region of a real-world-scale object that is either larger or smaller than a display voxel. A "voxel" may represent a three-dimensional region of the image-able field of any real-world size, and in some cases may represent a region smaller than any resolvable object of the imaging system. Voxels may be, but need not necessarily be three-dimensional square or rectangular prisms. Voxels may have any shape allowing for contiguous three-dimensional representation of the image-able field. In some cases, data representing a voxel may not be displayed, but may still be processed as a unit and referred to as a "voxel."

As used herein, the terms "pixel location" and "voxel location" (or "position") refer to a location within the image-able field that is identifiable by a coordinate system, which may be a Cartesian coordinate system or any other coordinate system.

As used herein, a "pixel" may be described as "intersecting" a "voxel." A two-dimensional pixel may be defined as intersecting a three-dimensional voxel using any desired convention. For example, for square pixels and cubic voxels, a pixel intersecting a voxel may be a square face of the voxel or any other square or rectangle passing through the voxel. If a coordinate system used for pixels is different than a coordinate system used for voxels, then one pixel may intersect multiple voxels.

As used herein, the term "echo" refers to an ultrasound wavefront or an analog or digital representation of an ultrasound wavefront that arrives at a receive transducer element. Because imaging methods described herein allow for an extremely wide range of probe configurations, some ultrasound signals arriving at a receive transducer may originate at a transmit transducer element on an opposite side of an imaged object. Such wavefronts are also intended to be included within the definition of an "echo" even if such wavefronts may also be described as "transmitted" or "deflected."

As used herein, the terms "reflector" and "scatterer" refer to a physical portion of a physical object being imaged. When struck by a wavefront, reflectors and scatterers will tend to re-radiate a wavefront in a direction generally dictated by physics. The terms are not intended to limit the relative geometry or positions of transmitters, scatterers, and reflectors.

As used herein, the verb terms "reflect" and "scatter" refer to the effect of a scatterer on a propagating ultrasound wavefront. In some cases, a wavefront that is only slightly deflected (e.g., forming a combined transmit element/scatterer/receive element angle approaching 180°) by a scatterer may still be described as having been "reflected" by that scatterer (or "reflector").

As used herein, the term "sample" refers to a digital data element in a physical volatile or non-volatile storage medium. Unless context suggests otherwise, "samples" described herein generally refer to data elements representing a discrete portion of a received ultrasound waveform. A time-varying electrical signal produced by a transducer element vibrating in response to a received ultrasound wavefront may be quantified and digitally sampled at a sample rate in order to produce a series of digital values representing the received time-varying electrical signal. Those values may be referred to as "samples." In some cases, a "sample" may include an interpolated value in between two digitally stored sample values.

If digital sampling is done at a known sample rate (usually, but not necessarily a consistent sample rate), the position of each sample (e.g., as measured by a location in memory device, or a position in a sequence of values) may be directly related to an arrival time of the wavefront segment responsible for each sample value.

As used herein, the term "beamform" refers to the process of determining a value for pixels or voxels based on a sample value (directly stored or interpolated), the known acoustic center position of a transmit element responsible for the sample value, and the known acoustic center position of a receive element responsible for the sample value. Beamforming is described in further detail elsewhere herein.

As used herein, the term "image" (as a noun) refers to a human-visible graphical representation of a physical object or a series of non-transitory digital values stored on a physical storage medium that may be interpreted by software and/or an image processor to produce such a graphical representation. As used herein, the term "image" does not necessarily imply any particular degree of quality or human-readability. An "image" may refer to a two-dimensional representation (e.g., a cross-section, in some cases) or a three-dimensional volumetric representation of an object. As used herein, the terms "image" and "imaging" (in verb form) refer to a process that results in an image.

Introduction to Point-Source Transmission Ultrasound Imaging

In various embodiments, point-source transmission ultrasound imaging, otherwise referred to as ping-based ultrasound imaging, provides several advantages over traditional scanline-based imaging. Point-source transmission differs in its spatial characteristics from a "phased array transmission" which focuses energy in a particular direction from the transducer element array along a directed scanline. A point-source pulse (also referred to herein as a "ping") may be transmitted so as to generate either a two-dimensional circular wavefront or a three-dimensional spherical wavefront, thereby insonifying as wide an area as possible in the two-dimensional or three-dimensional region of interest. Echoes from scatterers in the region of interest may return to all of the elements of receive apertures (or all of those elements not blocked by obstacles preventing transmission of the echoes). Those received echo signals may be filtered, amplified, digitized and stored in short term or long term memory (depending on the needs or capabilities of a particular system).

Images may then be reconstructed from received echoes by determining positions of reflectors responsible for received echo samples. The position of each reflector responsible for a digital echo sample may be calculated based on the arrival time of the received echo sample (which may be inferred based on a sample position), the acoustic position of the transmit element responsible for the echo sample, and the acoustic position of the receive element responsible for the echo sample.

Beamforming may be performed by a software-based, firmware-based, or hardware-based dynamic beamforming technique, in which a beamformer's focus may be continuously changed to focus at a particular pixel position corresponding to a reflector position. Such a beamformer may be used to plot the position of echoes received from point-source pings. In some embodiments, such a dynamic beamformer may plot the locus of each echo signal based on a round-trip travel time of the signal from the transmitter to an individual receive transducer element.

In the two-dimensional imaging case, for a given echo sample produced by a transmit transducer element and a receive transducer element, the locus of possible positions of the target reflector responsible for the echo sample will be an ellipse mathematically defined by two foci. A first focus of the ellipse will be at the position of the transmit transducer element and the second focus will be at the position of the receive transducer element. Although several other possible reflector positions lie along the same ellipse, echoes of the same target reflector will also be received by other receive transducer elements. The slightly different positions of each receive transducer element means that each receive element will define a slightly different ellipse for the target reflector. Accumulating the results by summing the ellipses for multiple elements will indicate an intersection of the ellipses for a reflector. As echo samples from more receive elements are combined with the first, the intersecting ellipses will converge towards a point at which the target reflector is located. The target reflector position may be correlated with a pixel location representing the reflector. The combined sample values may be used to determine a display intensity for a display pixel at the pixel location. The echo amplitudes received by any number of receive elements may thereby be combined to form each pixel. In other embodiments the computation can be organized differently to arrive at substantially the same result.

Various algorithms may be used for combining echo signals received by separate receive elements. For example, some embodiments may process echo-signals individually, plotting each echo signal at all possible locations along its ellipse, then proceeding to the next echo signal. Alternatively, each pixel location may be processed individually, identifying and processing all echo samples potentially contributing to that pixel location before proceeding to the next pixel location.

Image quality may be further improved by combining images formed by the beamformer from one or more subsequent transmitted pings, transmitted from the same or a different point-source (or multiple different point-sources). Still further improvements to image quality may be obtained by combining images formed by more than one receive aperture.

An important consideration is whether the summation of images from different pings, different transmit point-sources or different receive apertures should be coherent summation (phase sensitive) or incoherent summation (summing magnitude of the signals without phase information).

The decision as to whether to use coherent or incoherent summation may be influenced by the lateral extent/size of the receive aperture(s) and/or the transmit aperture(s). In some embodiments, it may be convenient to confine the size of an aperture to conform to the assumption that the average speed of sound is substantially the same for every path from a scatterer to each element of the receive aperture. For narrow receive apertures this simplifying assumption is easily met. However, as the width of the receive aperture increases, an inflection point may be reached (referred to herein as the "maximum coherent aperture width" or "maximum coherence width"), beyond which paths traveled by echoes of a common reflector will necessarily pass though different types of tissue having intrinsically different speeds of sound when returning to the elements furthest apart from one another. When this difference results in receive wavefront phase shifts approaching or exceeding 180 degrees, additional receive elements extended beyond the maximum coherence width will actually degrade the image rather than improve it.

The same considerations may also apply to the size of transmit apertures, which may include a plurality of coherently combined transducer elements. In the case of two-dimensional transducer arrays used in three-dimensional imaging (or 3D data collection), it may be useful to define a maximum coherent aperture size in two dimensions. Thus, in various embodiments a maximum coherent aperture may be defined as a group of transducer elements in a square, circle, polygon or other two-dimensional shape with a maximum distance between any two elements such that phase cancellation will be avoided when echo data received at the elements of the aperture are coherently combined.

Therefore, in order to realize the benefits (e.g., in terms of increased spatial resolution) of a wide probe with a total aperture width far greater than the maximum coherent aperture width, the full probe width may be physically or logically divided into multiple receive apertures, each of which may be limited to an effective width less than or equal to the maximum coherent aperture width, and thus small enough to avoid phase cancellation of received signals.

The maximum coherence width can be different for different patients (or different test objects), for different probe positions on the same patient, and for other variables such as ultrasound frequency. In some embodiments, a compromise width may be determined for a given probe and/or imaging system. In other embodiments, a multiple aperture ultrasound imaging control system may be configured with a dynamic algorithm to subdivide the available elements into groups that are small enough to avoid significant image-degrading phase cancellation. In various embodiments, a particular coherent aperture size may be determined automatically by a control system, or manually through user input via a user control such as a dial or slider.

In some embodiments, coherent (phase sensitive) summation may be used to combine echo data received by transducer elements located on a common receive aperture resulting from one or more pings. In some embodiments, incoherent summation may be used to combine echo data or image data received by separate receive apertures if such receive apertures are sized and positioned so as to form a combined total aperture that is greater than a maximum coherence width for a given imaging target.

Two-dimensional ping-based beamforming may implicitly assume that the wavefronts emitted from the point-source are physically circular in the region of interest. In actuality, the wavefront may also have some penetration in the dimension orthogonal to the scanning plane (i.e., some energy may essentially "leak" into the dimension perpendicular to the desired two-dimensional image plane, which may have the effect of reducing the effective imaging depth). Additionally, the "circular" wavefront may actually be limited to a semicircle or a fraction of a circle less than 180 degrees ahead of the front face of the transducer according to the unique off-axis properties of the transducing material used. Similarly, a three-dimensional "spherical" wavefront may have an actual shape of a hemisphere or less than a hemisphere within the medium to be imaged.

Point-Source Transmission for 3D Ultrasound Imaging

The above description of point-source ultrasound imaging (also referred to herein as "ping-based" imaging) predominantly describes two-dimensional imaging in which ultrasound signals are focused into a narrow field approximating a plane in a region of an image. Such two-dimensional focusing may be accomplished with lensing or other techniques. Ping-based imaging can also be extended to real-time three-dimensional imaging without adding significant complexity. Three-dimensional ping-based imaging can be performed using an ultrasound probe with transducer elements spaced from one another in two dimensions. Some example probe configurations are described elsewhere herein.

When a three-dimensional pulse is initiated from a point-source transmit transducer, the resulting semi-spherical wavefront travels into the region of interest (ROI) where some of the ultrasound energy may be reflected (or deflected) by scatterers in the ROI. Some of the echoes from the scatterers may travel towards receive transducer elements of the probe, where the echoes may be detected, amplified, digitized, and stored in a short-term or long-term memory device. Each digitized sample value may represent a scatterer from the ROI. As in the 2D case, the magnitude of each received sample, along with its time of arrival and the exact positions of the transmit and receive transducers used, may be analyzed to define a locus of points identifying potential positions of the scatterer. In the 3D case, such a locus is an ellipsoid having as its foci the positions of the transmit and receive transducer elements. Each unique combination of transmit and receive transducer elements may define a separate view of the same reflector. Thus, by combining information from multiple transmit-receive transducer element combinations, the actual location of each reflector may be more accurately represented.

For example, in some embodiments an image in a 3D array of voxels may be assembled in computer memory by beginning with an evaluation of a selected digital sample. The selected digitized sample value may be written into every voxel indicated by the corresponding ellipsoid described above. Proceeding to do the same with every other collected sample value, and then combining all resulting ellipsoids may produce a more refined image. Real scatterers would be indicated by the intersection of many ellipsoids whereas parts of the ellipsoids not reinforced by other ellipsoids would have low levels of signal and may be treated as noise (i.e., eliminated or reduced by filters, gain adjustments, or other image processing steps).

In other embodiments, the order of computation may be changed by beginning with a selected voxel in a final 3D image volume to be produced. For example, for a selected voxel, the closest stored sample or interpolated sample may be identified for each transmitter/receiver pair. All samples corresponding to the selected voxel may then be evaluated and summed (or averaged) to produce a final representation of the voxel. Closeness of a sample to a selected voxel may be determined by calculating the vector distance from the three-dimensional position of a transmitter (i.e., the transmitter used to produce the sample) to the selected voxel position plus the vector distance from the selected voxel position to the position of a receiver used to produce the sample. Such a linear distance may be related to the time-divided sample values by dividing the total path length by speed of sound through the imaged object. Using such a method, the samples corresponding to a calculated time may be associated with the selected voxel.

Image Layer Combining

Techniques for determining the location for received echo samples are generally referred to herein as beamforming, while techniques for combining information obtained from multiple transmitter/receiver combinations or from multiple separate pings transmitted using the same transmitter/receiver combination may generally be referred to as image layer combining. In various embodiments, a frame may be made up of any number of combined image layers. Frames may be displayed sequentially at a desired frame-rate on a display to form a moving image or video. The above-described beamforming processes may beneficially also be used for evaluating pixel values in a 2D cross-sectional slice through a 3D volume using raw echo data. In various embodiments, such 2D slices may be taken at any arbitrary angle or along any curved path through the 3D volume. The same techniques may also be used to zoom in (i.e., increase the size of features) using raw echo data rather than enlarging processed pixels or voxels.

Images obtained from different unique combinations of one ping and one receive element and/or combinations of one ping and one receive aperture may be referred to herein as "sub-image layers." Multiple sub-image layers may be combined coherently to improve overall image quality. Additional image layer combining may be performed to further improve the quality of a final image. In the context of image layer combining, the term "image" may refer to a single two-dimensional pixel, a single voxel of a three-dimensional volume or a collection of any number of pixels or voxels.

Image layer combining may be described in terms of four image layer levels. These three cases include base-level image layers, first-level image layers, second-level image layers and third-level image layers. As used herein, the phrase base-level image layer refers to an "image" obtained by beamforming echoes received at a single receive element from a single transmitted ping. As described above, the beamforming process defines an ellipse corresponding to each echo sample. Therefore, a base-level image may consist of a series of such ellipses representing all of the echoes of a single ping received by a single receive element. Such an image may not be particularly useful for diagnostic imaging purposes, but may be used for other purposes.

A first-level image layer may be formed from echoes received at a single receive aperture resulting from a single ping from a single transmit aperture (where a "transmit aperture" can be a single apparent point-source transmit element, a single-element transmitter, or a group of transmit elements). For a unique combination of a single ping and a single receive aperture, the echoes received by all the receive elements in the receive aperture may be summed coherently to obtain a first-level image layer. Alternatively, first-level images may be formed by combining the echoes of two or more pings received at elements of a common receive aperture.

Multiple first-level image layers resulting from echoes of multiple transmit pings (from the same or different transmit apertures) received at a single receive aperture can be summed together to produce a second-level image layer. Second-level image layers may be further processed to improve alignment or other image characteristics.

Third-level images may be obtained by combining second-level image layers formed with data from multiple receive apertures. In some embodiments, third-level images may be displayed as sequential time-domain frames to form a moving image.

In some embodiments, pixels or voxels of a first-level image layer may also be formed by summing in-phase and quadrature echo data, that is by summing each echo with an echo ¼ wavelength delayed for each receive-aperture element. In some cases, echo data may be sampled and stored as an in-phase data set and as a separate quadrature data set. In other cases, if the digital sampling rate is divisible by four, then a quadrature sample corresponding to an in-phase sample may be identified by selecting a sample at an appropriate number of samples prior to the in-phase sample. If the desired quadrature sample does not correspond to an existing whole sample, a quadrature sample may be obtained by interpolation. Combining in-phase and quadrature data for a single image (pixel, voxel or collection of pixels or voxels) may provide the advantage of increasing the resolution of the echo data without introducing blurring effects. Similarly, samples at values other than ¼ wavelength may be combined with in-phase samples in order to improve various imaging characteristics.

Combination, summation or averaging of various image layers may be accomplished either by coherent addition, incoherent addition, or a combination of the two. Coherent addition (incorporating both phase and magnitude information during image layer summation) tends to maximize lateral resolution, whereas incoherent addition (summing magnitudes only and omitting phase information) tends to average out speckle noise and minimize the effects of image layer alignment errors that may be caused by minor variations in the speed of sound through the imaged medium. Speckle noise is reduced through incoherent summing because each image layer will tend to develop its own independent speckle pattern, and summing the patterns incoherently has the effect of averaging out these speckle patterns. Alternatively, if the patterns are added coherently, they reinforce each other and only one strong speckle pattern results.

In most embodiments, echoes received by elements of a single receive aperture are typically combined coherently. In some embodiments, the number of receive apertures and/or the size of each receive aperture may be changed in order to maximize some desired combination of image quality metrics such as lateral resolution, speed-of-sound variation tolerance, speckle noise reduction, etc. In some embodiments, such alternative element-to-aperture grouping arrangements may be selectable by a user. In other embodiments, such arrangements may be automatically selected or developed by an imaging system.

Variations in the speed of sound may be tolerated by incoherent addition as follows: Summing two pixels coherently with a speed-of-sound variation resulting in only half a wavelength's delay (e.g., approximately 0.25 mm for 3 MHz ultrasound) results in destructive phase cancellation, which causes significant image data loss; if the pixels are added incoherently, the same or even greater delay causes only an insignificant spatial distortion in the image layer and no loss of image data. The incoherent addition of such image layers may result in some smoothing of the final image (in some embodiments, such smoothing may be added intentionally to make the image more readable).

At all three image layer levels, coherent addition can lead to maximum lateral resolution of a multiple aperture system if the geometry of the probe elements is known to a desired degree of precision and the assumption of a constant speed of sound across all paths is valid. Likewise, at all image layer levels, incoherent addition leads to the best averaging out of speckle noise and tolerance of minor variations in speed of sound through the imaged medium.

In some embodiments, coherent addition can be used to combine image layers resulting from apertures for which phase cancellation is not likely to be a problem, and incoherent addition can then be used where phase cancellation would be more likely to present a problem, such as when combining images formed from echoes received at different receive apertures separated by a distance exceeding some threshold.

In some embodiments, all first-level images may be formed by using coherent addition of all sub-image layers obtained from elements of a common receive aperture, assuming the receive aperture has a width less than the maximum coherent aperture width. For second and third level image layers, many combinations of coherent and incoherent summation are possible. For example, in some embodiments, second-level image layers may be formed by coherently summing contributing first-level image layers, while third-level image layers may be formed by incoherent summing of the contributing second-level image layers.

Time-domain frames may be formed by any level of image layer depending on the desired trade-off between processing time and image quality. Higher-level images will tend to be of higher quality, but may also require more processing time. Thus, if it is desired to provide real-time imaging, the level of image layer combination processing may be limited in order to display images without significant "lag" being visible to the operator. The details of such a trade-off may depend on the particular processing hardware in use as well as other factors.

[reference to other applications describing 2D and 3D ping based imaging: 711 and 710]

2D Imaging while Collecting 3D Data

In some embodiments, a form of 2D imaging may be performed using a probe and imaging system configured for 3D imaging by simply beamforming and displaying only a 2D slice of data from the received three-dimensional echo data. For example, such techniques may be used in order to reduce a beamform calculation and simplify display for real-time imaging using an imaging device with limited processing capability, while still retaining the full 3D echo data.

For example, a two-dimensional plane may be selected (automatically or by a user) from the voxels making up a three-dimensional volumetric representation of the imaged region, voxels intersecting the selected plane may be identified. A two-dimensional image of the selected plane may then be formed by beamforming only those echo samples corresponding to the voxels intersecting the selected plane. The selected two-dimensional image plane may then be displayed in real-time while three-dimensional data of the entire insonified volume is simultaneously collected.

The collected full 3D echo data may be beamformed and reviewed at a later time using a device with greater processing power. In some embodiments, the 2D slice to be beamformed and displayed may be automatically selected by an imaging device. Alternatively, the 2D slice to be beamformed and displayed may be selected or adjusted by an operator of the device.

Data Capture & Offline Analysis

In various embodiments, raw un-beamformed echo data resulting from a ping transmitted from point-source transmit transducers and received by one or more arrays of receive transducer elements may be captured and stored in a raw data memory device for subsequent retrieval and analysis. Alternately, captured echo data may be digitally transmitted over a network for remote processing, beamforming, and/or viewing. In addition to echo data, additional data may also be stored and/or transmitted over a network and retrieved for subsequent and/or remote image generation and analysis. Such additional data may include calibration data describing the positions of the transmitting and receiving transducer elements, and transmit data describing the identity (or position) of transmitting transducers associated with specific echo data.

After retrieving such data, a clinician may use the data to reconstruct imaging sessions in a variety of ways while making adjustments that may not have been made during a live imaging session. For example, images of a series of 2D slices through a 3D volume may be generated and shown in succession in order to simulate a 2D transducer passing across a surface of the region of interest. Examples of these and other methods are described in Applicant's US Patent Application Publication 2014/0058266, titled, "Ultrasound Imaging System Memory Architecture" and PCT Patent Application Publication WO2016/028787, titled "Network-Based Ultrasound Imaging System.".

Some embodiments of a probe configured for imaging an entire patient's body or a substantial portion of a patient's body may comprise an array of apparent point-source transmitters and receive elements sized to cover a substantial portion of the desired region of a patient's body. For example, a probe may be sized to cover substantially half of a patient's chest or more. Such a probe may have a maximum dimension of about 8 cm to about 10 cm.

Alternatively, a much smaller probe capable of insonifying a conically-shaped volume of, for example, + or −30 degrees, can be placed on a patient's body such that an organ of interest may be included in the cone. Such a probe may be placed in more than one place to cover a larger volume of interest.

Detecting Motion of Objects in Imaged Medium

In certain medical and non-medical applications, it may be desirable to monitor the position and very small movements of structures within an imaged medium to a high degree of precision and accuracy, with very low latency (i.e., very fast response). In general, systems and methods for achieving these goals may be referred to herein as motion detection and/or motion tracking. For example, in certain robotic surgery applications, it is desirable to detect and respond to very small movements of a body part on which surgery is being performed so as to minimize injury or damage. Various systems and methods of achieving high-reliability object motion detection and motion tracking using ping-based multiple aperture ultrasound will now be described with reference to FIG. 1-FIG. 6.

Approaches to such a challenge may depend on available ultrasound imaging hardware. For example, in some cases, an ultrasound probe configured to image a target object using one or more arrays of apparent-point-source transmitters interspersed with geometric receive elements, or any other probe configured for ping-based ultrasound imaging, may be suitably used for detecting and tracking motion with high speed, precision and accuracy. Other embodiments may involve use of a probe, an imaging system, and a user interface specifically configured for motion detection and/or motion tracking applications. Examples of various probe and imaging system configurations used for motion tracking are provided below.

An overview of example approaches to motion detection and motion tracking will now be provided, followed by particular examples of systems and methods that may be used for performing motion detection and motion tracking. Various embodiments of processes for detecting motion of one or more objects, areas, or regions within an insonified region will be described with reference to FIG. 1, and various embodiments of processes for tracking motion will be described with reference to FIG. 2.

As used herein, the phrase "motion detection" or "motion monitoring" may refer a process for establishing a binary (e.g., "no motion" vs. "motion") determination of whether or not motion of one or more watched points has occurred. Motion detection may refer to indications of motion of one or more objects, points, or other defined regions within an insonified plane or volume.

As used herein, the term "motion tracking" may refer to the collection, determination, or calculation of one or more metrics describing detected motion. For example, motion tracking may comprise an indication of the speed of a moving object, an indication of a new position, relative to some coordinate system, of an object that has moved, or other metrics describing the moving or moved object. In some cases, motion may be detected and/or tracked in six degrees of freedom. For example, linear motion in x, y, and z directions as well as The process flow diagram of FIG. 1 illustrates an example of a motion detection process 400 comprising the steps of: obtaining an image of an object (or multiple objects) to be tracked 402 within a medium, selecting a plurality of fiducial regions on or in the object to be tracked 404, defining one or more fingerprints within each fiducial region 405, transmitting a series of tracking pings into the medium 406; identifying each fiducial region or a portion of each fiducial region in the un-beamformed receive echo data 408, monitoring a position of each fiducial region within the un-beamformed echo data 410, detecting a shift in position of at least one of the fiducial regions within the un-beamformed echo data 412, and producing a signal indicating that motion has occurred 414.

In some embodiments, obtaining an image of the object to be tracked 402 may comprise obtaining one or more two-dimensional images of an object to be tracked within a medium. For example, the imaging system may be configured to display at least two planar (two-dimensional) images of the medium including the object (or objects) to be monitored for motion. The first image plane may be oriented at an angle relative to the second image plane. The first and second image planes may be orthogonal to one another or at some other angle, but the first and second image planes are preferably not co-planar.

The imaging system may also be configured to indicate regions of the first and second image planes that overlap one another. If desired, a user may move the probe relative to the object being imaged so as to re-position a target object within the first and second image planes. In some embodiments, only a single image plane may be required for identifying and/or selecting a plurality of fiducial regions.

In some embodiments, rather than displaying two dimensional slices, the system may produce and display a three-dimensional rendering of the imaged region, including one or more objects to be monitored and tracked.

Selecting Fiducial Regions and Fingerprints

As used herein, the terms "fiducial region," and "fiducial point" may refer to a small region of space (which may be two-dimensional or three-dimensional) within an insonified area or volume which may be represented by an imaging system. While a fiducial region may in some cases be selected based on an image displayed on a human-visible or human-readable display device, the fiducial region itself may also exist as a defined data set produced by an imaging system from which a visible image may be produced if desired. In other words, a fiducial region need not (but may) equate to an image. In some embodiments, a fiducial region may be selected without displaying an image.

As used herein, a "fingerprint" or a "fingerprint point" may be a machine-recognizable signature representing all or a portion of a fiducial region. Specific examples of fingerprints are described elsewhere herein. In some cases, a defined fiducial region may be sized to be large enough to be a human-visible dot in a displayed image of the imaged region. In some cases, such a fiducial region may be larger than needed or desired for high-speed motion detection and tracking. Therefore, in some cases it may be desirable to define a fingerprint that represents a much smaller machine-recognizable region within a fiducial region.

In some cases, an entire fiducial region dataset or image may be processed and automatically analyzed as a fingerprint representing a region within the imaged region as perceived by the imaging system. In such embodiments, an entire fiducial region selected at block 404 may be defined as the fingerprint at block 405.

In some cases, a fingerprint may comprise a two-dimensional or three-dimensional portion of a fiducial region which may be referred to as "a sub-region," "a sub-volume," "a sub-area," may be defined within a fiducial region so as to establish a machine-recognizable signature representing a portion of a larger fiducial region. In such cases, defining fingerprints in fiducial regions as indicated at block 405 may include defining a sub-region of the fiducial region as a fingerprint. For example, a portion of a fiducial region may be selected as a fingerprint that may be used to consistently identify the fiducial region.

In some embodiments, a fingerprint may comprise one or more strings of data samples representing a section of a complete data set representing a fiducial region. A complete data set representing a fiducial region may be made up of all echo data samples that may be mapped (e.g. by a beamforming process) to points within a fiducial region. In some embodiments, a fingerprint may be defined by data points representing non-contiguous points or contiguous points within a fiducial region. A fingerprint defined as a sub-region of a fiducial region may also be defined in terms of a collection of data samples that make up the points in the sub region.

In some cases, the step of defining fiducial regions may comprise defining regions suitable as fingerprints, thereby negating the need for a separate step for defining fingerprints within fiducial regions.

In various embodiments, the step of selecting a plurality of fiducial regions on or in the object to be tracked 404 may comprise automatic or manual selection of one, two, three, or more small regions. In some embodiments, three fiducial regions may be selected. Selection of at least three non-linear fiducial regions may beneficially facilitate the ability to detect and/or track motion in six degrees of freedom. Because the position of each of the three points may be known relative to one another and relative to the probe, any motion of an object may be detected and tracked in six degrees of freedom.

In some embodiments, selecting a fiducial region may comprise a human user or an automated software agent identifying and selecting a particular region for use as a fiducial region. Similarly, selection and/or definition of a fingerprint within a fiducial region may be performed manually by a human user or automatically by an automated software agent. In some cases, selection of fiducial regions and fingerprints may be semi-automated while being directed by a human user. For example, a user may place a cursor or pointer at a desired location on a display, and an automated system may select a fiducial region and/or a fingerprint at pre-determined locations relative to the cursor or pointer. A software agent may be configured to select a fiducial region and/or a fingerprint based on pre-determined criteria, or based on criteria defined by a human user. In cases in which fiducial regions and fingerprints are selected and defined automatically, the step 402 of obtaining an image may be omitted.

In some embodiments, defining a fiducial region and/or a fingerprint may include defining one or more datasets (made up of group of echo data samples) associated with a corresponding region on or within an object and with a corresponding portion of an image displayable on a display screen. A dataset representing a fiducial region or a fingerprint may include digitized data received by one or more receive transducer elements of an imaging system. In some cases, a data set representing a fiducial region or a fingerprint may include data obtained by combining data received by more than one transducer element. For example, data representing a fiducial region or a fingerprint may include coherently combined data received by a plurality of transducer elements making up a receive aperture. In other embodiments, data representing a fiducial region or a fingerprint point may include coherently combined or incoherently combined data received by two or more receive apertures or elements.

Therefore, in some embodiments, a fiducial region may be defined (manually by a human user or automatically by an imaging system or other computing system), and the step of defining a fingerprint within the fiducial region may comprise defining a sub-region within the fiducial region (manually or automatically), and then defining the fingerprint as a collection of data samples from among a complete data set representing the entire sub-region. Alternately, the step of defining a fingerprint within the fiducial region may comprise directly defining a collection of data samples from among a complete data set representing the entire fiducial region.

In some embodiments, a fingerprint defined as a collection of data samples may be beneficial in performing a motion detection process by monitoring a sample-position of a fingerprint in un-beamformed data.

In some embodiments, fingerprint echo sample datasets may be defined based on echoes received by at least two receive elements that are spaced apart from one another by a significant distance. For example, in some embodiments fingerprint-defining receive elements may be selected such that rays drawn from the selected receive elements to a selected fingerprint point (or fiducial region) form an angle as close to 90° as possible. Receive elements for defining a fingerprint data set may be selected based on a distance between the elements. For example, a fingerprint data set may be defined as echo data corresponding to a selected fingerprint received by two elements that are spaced from one another by at least X cm, where X may be at least 2 cm, at least 3 cm, at least 4 cm, at least 5 cm, at least 6 cm or more.

In some embodiments, a fingerprint may comprise one or more recognizable peaks and/or troughs, which may be indicative of a hard reflector and/or a transmitted ping pattern that may produce distinct peaks and/or troughs in echo signals. In some cases, peaks or troughs may be recognizable in raw un-beamformed echo data based on local maxima or minima in the echo data.

In various embodiments, the physical size of a region defined by a fiducial region or a fingerprint point (or both) may be anywhere from a small fraction of a square millimeter to several square centimeters or more, depending on various factors such as the physical size of a transducer or transducer array used by the imaging system and the size of the imaged object itself. In an example medical imaging case, an ultrasound imaging transducer array may have a size on the order of about 1 square centimeter to about 100 square centimeters, and a fiducial point may represent a physical region on the order of about one square millimeter, $0.1$ mm$^2$, $0.0625$ mm$^2$, $0.05$ mm$^2$, or less.

In some cases, a fiducial region or a fingerprint (or both) may represent a region much smaller than any resolvable object for a particular imaging system. In other words, a fiducial region or a fingerprint point need not represent an actual visible structure within an imaged object. In such cases the fiducial region or fingerprint may actually contain artifacts, noise or other distortions and/or characteristics of the imaging system at the selected point within the imaging field. In some cases, a fiducial region or a fingerprint may comprise multiple reflectors, while in other cases, a fiducial region or a fingerprint may contain a single reflector, or no human-visible reflectors. If the imaging system being used for motion detection or motion tracking is based on transmitted ultrasound or other energy, then a fiducial region may contain no reflectors at all.

In some embodiments, defining a fingerprint point may comprise defining a point with a maximum dimension (e.g., a circular diameter, a rectangular diagonal dimension, etc.) that is less than half of a size of a smallest detail resolvable by an imaging system. In some embodiments, defining a fingerprint point may comprise defining a point with a maximum dimension that is less than a quarter of a size of a smallest detail resolvable by an imaging system. In some embodiments, defining a fingerprint point may comprise defining a point with a maximum dimension that is less than a tenth of a size of a smallest detail resolvable by an imaging system.

In some embodiments, defining a fingerprint point may comprise defining a point with a maximum dimension that is less than half of a wavelength of ultrasound transmitted by the imaging system. In some embodiments, defining a fingerprint point may comprise defining a point with a maximum dimension that is less than a quarter of a wavelength of ultrasound transmitted by the imaging system. In some embodiments, defining a fingerprint point may comprise defining a point with a maximum dimension that is less than a tenth of a wavelength of ultrasound transmitted by the imaging system. In some embodiments, defining a fingerprint point may comprise defining a point with a maximum dimension that is less than a hundredth of a wavelength of ultrasound transmitted by the imaging system.

Each fiducial region and/or fingerprint may comprise a small region known to be on a surface of or inside of the object to be tracked. For example, if the object to be tracked is a bone (such as a femur, tibia, fibula, patella, etc.), then the selected fiducial region and/or a fingerprints may be on the surface of the bone, inside of the compact bone, inside the spongy bone, or in the bone marrow. Such features may be visible and recognizable to an operator in an image produced by a ping-based multiple aperture ultrasound imaging system as described herein, or in other imaging systems.

In some embodiments, features identifying a target object to be tracked may be automatically recognized by a suitably trained neural network or other computer aided detection system. Fiducial regions and/or fingerprints s may also be identified on a surface of or inside of soft tissues, organs, muscles, cartilage, fluids, surgical implements, needles, catheters, robotic surgery devices or any other identifiable structure or substance.

In some embodiments, it may be desirable to select regions with a high degree of contrast for use as fiducial regions and/or fingerprints. For example, in such embodiments, a fiducial region and/or fingerprint point may comprise a dark region surrounded by whiteness, or a substantially white region surrounded by darkness. In other embodiments, regions of any visible contrast level may be used as fiducial regions and/or fingerprint points. In some embodiments, the analysis of fiducial regions and/or fingerprint points may occur on a scale smaller than any visible structure, so human-visible contrast may not be important as long as the selected fiducial point or fingerprint point contains features discernable to the processing system.

Fiducial regions and/or fingerprint points may be of any desired shape, such as square, rectangular, circular, or amorphous shapes. Fiducial regions and/or fingerprint points may also be of any desired size. For example, a fiducial region and/or a fingerprint point may comprise an area of less than one square millimeter, a few square millimeters, several square millimeters in size, or larger.

For example, a fiducial region or a fingerprint point may comprise an amorphous area of approximately 1 mm, 0.5 mm, 0.25 mm, 0.022 mm in diameter or smaller. In another example, a fiducial region or a fingerprint point may comprise a square or rectangular area of about one to 100 square nanometers or smaller. In some embodiments, the fingerprint point may be a square, rectangle, circle or other shape with sides or diameter that is a multiple or a fraction of the wavelength ($\lambda$) of transmitted ultrasound signals. For example, a fingerprint point may have a side or diameter about equal to $\lambda$, $2\times\lambda$, $3\times\lambda$, $4\times\lambda$, or larger multiples of the wavelength, or $0.75\lambda$, $0.5\lambda$, $0.25\lambda$ or smaller.

In some embodiments, fiducial regions or fingerprint points may be beneficially separated from one another by about 1 mm to about 100 mm or more for an object in a human patient. In veterinary patients or industrial applications, much greater distances between points may be used, such as up to 1 meter or up to 10 meters or more. In other embodiments, fingerprint points may be beneficially separated from one another by as much as the full extents of the image planes. The full extent of the image planes may depend on factors such as the size of the probe being used, the zoom level, and other factors. Greater separation between points may allow for greater sensitivity in detecting movement of the object.

Selection of fiducial regions or fingerprint points may be manual such as by a human operator selecting one or more points via a user-interface device. For example, a user may select a first fiducial region or fingerprint point in the region in which the first image plane overlaps the second image plane. If no suitable point can be identified in the overlap region, the probe may be re-positioned until a point suitable for use as a fiducial region or fingerprint point lies in the intersection region. A user may select a second fiducial region or fingerprint point in the first image plane. A user may select a third fiducial region or fingerprint point in the second image plane. In other example embodiments, the first fiducial region or fingerprint point may be in a region of the first or second image plane other than in the overlapping region. In still other example embodiments, the first fiducial region or fingerprint point may lie on a third image plane that is not coplanar with either the first image plane or the second image plane.

Alternatively, selection of fiducial regions or fingerprint points may be partially or entirely automated, such as by software evaluation of one or more images so as to automatically identify and select points meeting a set of predetermined criteria such as those discussed above, or other criteria.

For example, in some embodiments, selecting multiple fiducial regions or fingerprint points may comprise positioning a point selection icon on an object of interest in a displayed image of the object. A point selection icon may comprise a two dimensional shape, such as a triangle, an equilateral triangle, a square, a rectangle or another polygonal shape. Each vertex or other point along linear segments of a polygonal point selection icon may represent a fiducial region or fingerprint point. Thus, in some embodiments, a user may manipulate a user interface to position a point selection icon on a desired region of an image of a target object, and a computer system may select suitable fiducial regions or fingerprint points from regions identified in relation to the icon, such as points within the polygonal shape, points at the vertices of the polygon, points along linear segments of the polygon, or other points defined in relation to the icon. In various embodiments, a point selection icon may include curved sections, amorphous shapes, circular shapes, elliptical shapes or other shapes.

In some embodiments, a size of a point selection icon may be adjusted by manipulation of a user interface device. Alternatively, a point selection icon may have a fixed distance between fingerprint-point-defining features. Spacing fiducial regions or fingerprint points at a significant distance from one another may provide for improved motion tracking.

Transmitting Tracking Pings

In various embodiments, the step of transmitting a series of tracking pings into the medium 406 may comprise transmitting pings at a pre-determined ping-repetition-rate from a single transmit element. In some embodiments, the single transmit element used for transmitting tracking pings may be an apparent point source transmitter (as described, for example, in US Patent Application Publication 2015/0080727, titled "Ultrasound Imaging Using Apparent Point-Source Transmit Transducer") or any other transmit transducer or combination of transducer elements or microelements approximating a point-source. In other embodiments, the single transmit element used for transmitting tracking pings may be an element of a linear array. In other embodiments, tracking pings may be simultaneously or sequentially transmitted from two or more transmit transducer elements. In some embodiments, tracking-ping transmit transducer elements may be located in the same probe as the receive elements. In some embodiments, transmit transducer elements may be independent of a probe containing receive transducer elements.

As described above, in some cases, a fingerprint may comprise one or more peaks that may be identifiable in raw un-beamformed echo data. In such embodiments, each tracking ping may be transmitted with a waveform approximating an impulse. For example, the tracking ping transmitter may be driven with a triangular waveform with a single peak for each tracking ping. The returned echoes may have a recognizable peak with a sufficiently narrow spread in time that the peak of the received pulse may be distinguished with enough precision to identify a desired degree of motion. Any time-shift of the received peak may be related to a change in the distance between the object and the probe based on the speed-of-sound in the object. Thus, the precision with which the peak may be recognized may be related to the desired precision of motion detection.

In other embodiments, motion detection may be performed based on a monitored position of a fingerprint that may not necessarily contain one or more identifiable peaks, but may be a pattern of raw un-beamformed data that may be identifiable as a data string. In such embodiments, tracking pings need not have a significant peak and may have other signal shapes, such as a partial sinusoidal cycle, a full sinusoidal cycle, a sinusoidal half-cycle, a coded excitation signal shape, or partial or full cycles of any other shape. In such embodiments, rather than monitoring the position of a reflection peak, the motion detection process may monitor a position of a fingerprint as further described below.

Another important variable relating to ping transmission is the ping repetition rate. A maximum ping-repetition rate may be determined based on a given ultrasound frequency, a given maximum depth of the medium, a given speed-of-sound in the imaged medium, and an attenuation rate of ultrasound in the imaged medium. For given quantities of such variables (and/or others), a maximum ping-repetition rate may be defined by the maximum round-trip travel time required for a single ping to travel from the tracking ping transmit element(s) to the deepest point in the medium, and then return to the furthest receive element of the transducer array (where the deepest point may be defined at least partially based on a minimum acceptable signal-to-noise ratio for the returning echo signal). Echoes of a first ping may be most easily distinguished from echoes of a subsequent second ping if the second ping is transmitted no sooner than the maximum round-trip travel time after transmission of the first ping. Thus, in some embodiments, a pre-determined ping-repetition-rate may be the inverse of the maximum round-trip ping travel time for a particular ultrasound frequency, depth, and speed-of-sound. In other words, the pre-determined ping-repetition-rate may involve transmitting one ping every $t_{RT}$ seconds, where $t_{RT}$ is equal to the maximum round-trip ping travel time for a particular ultrasound frequency, depth, and speed-of-sound.

In alternative embodiments, tracking pings may be transmitted at a rate faster than the maximum round-trip ping travel time for a particular ultrasound frequency, depth, attenuation rate, and speed-of-sound. Transmitting tracking pings (or imaging pings) faster than the maximum round-trip ping travel time may allow for faster motion detection response times, faster motion tracking update times, and higher frame rates. Such higher ping-rates are possible by using various techniques, some examples of which are provided below.

In some embodiments, tracking pings may be transmitted at a rate faster than the maximum round-trip ping travel time for a particular ultrasound frequency, depth, attenuation rate, and speed-of-sound if the fiducial regions and/or fingerprint points are selected so as to all be within the same range of depth as one another. In such an embodiment, late-arriving echoes (e.g., from deep or distant reflectors) of a first ping may be indistinguishable from early-arriving echoes (e.g., from shallow or near-field reflectors) of a second subsequent ping.

Figure 3:
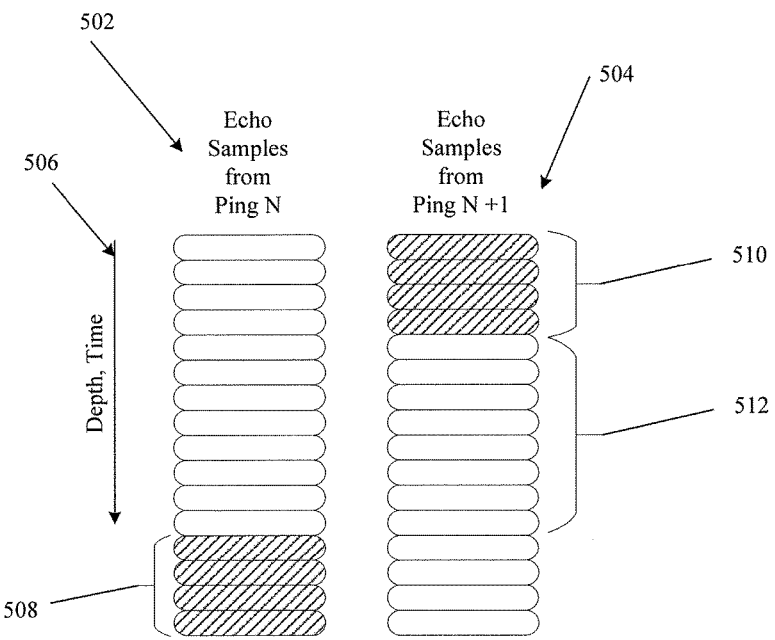
FIG. 3 is a diagram illustrating transmission of overlapping ping signals.

FIG. 3 schematically illustrates echoes received from two consecutively transmitted pings. The left column 502 includes a series of blocks, each representing a sample or a group of samples collected from echoes of a first ping, referred to as ping number "N". The blocks of the right column 504 represent samples collected from echoes of a subsequent ping transmitted immediately after ping N. In the illustration of FIG. 3, both depth (i.e., distance into the imaged object from the transmit element) and time from ping transmission are represented by the vertical axis 506. If the second ping (N+1) is transmitted at a time before the deepest echoes 508 from the first ping N are received, then the most shallow echoes 510 of the second ping N+1 will overlap in time with the deepest echoes 508 of the first ping N. If no other methods are available for distinguishing echoes of the first ping N from echoes of the second ping N+1, then the overlapping deep and shallow echoes 508 and 510 may interfere with one another, causing difficulties in imaging or motion tracking based on those overlapping echoes.

However, the echoes in a midfield region 512 between the deepest echoes 508 and the shallowest echoes 510 may be free of any overlaps. Therefore, by selecting fingerprint points that are known to lie in a mid-field region that is free from such overlapping echo returns, the tracking ping transmission rate may be increased above the round-trip ping travel time without degrading either a motion detection process or a motion tracking process. This mid-field region that is free of overlapping echoes of consecutive pings may be referred to herein as a "free depth range." As the ping repetition rate increases (i.e., as pings are transmitted with shorter time intervals between them), the size of the free depth range gets smaller.

Thus, in some embodiments, the selection of fiducial regions or fingerprint points may be constrained to a depth region that may be defined based on a desired tracking-ping transmission rate. A wider free depth range may correspond with a lower number of tracking pings per second, while a more narrow free depth range may allow for transmission of a higher number of tracking pings per second. In some embodiments, a free depth range within which fiducial regions or fingerprint points may be selected may be indicated to a user on a graphical display, or a user-interface may prevent a user from selecting fiducial regions or fingerprint points that lie outside of a determined free depth range. In some embodiments, a user may adjust a tracking ping transmission rate and/or a width of an allowable fingerprint point selection range. In cases of automatic selection of fiducial region or fingerprint points, the automated process may be configured to avoid selecting fiducial region or fingerprint points outside of the free depth range and to only select fiducial region or fingerprint points within the free depth range.

In some cases, ultrasound signals deeper than the "deepest" echoes shown in FIG. 3 may be assumed to be too attenuated to cause trouble due to overlaps. Because the attenuation rate of ultrasound varies with ultrasound frequency, the size of the free depth range may also be varied by varying the frequency of transmitted ultrasound pings. In the case of medical imaging, an attenuation rate in average human tissue is commonly accepted to be approximately 0.5 dB/MHz/cm of one-way travel. Attenuation rates for different media will tend to be different.

In some embodiments, a frequency of transmitted ultrasound may also be selected so as to minimize echoes from reflectors substantially deeper than the deepest end the free depth range. An ultrasound frequency may be selected based on an attenuation rate of ultrasound at that frequency in the medium to be imaged. Because higher frequency ultrasound attenuates with distance traveled at a higher rate than lower frequency ultrasound, a frequency may be selected at which echoes from regions substantially deeper than the free depth range are sufficiently attenuated before interfering with shallow echoes of the subsequent ping. Therefore, in some embodiments a tracking ping transmit frequency may be manually or automatically adjusted based on a size of a desired free depth range.

In some embodiments, imaging pings may also be transmitted at a rate greater than an inverse of the full round-trip travel time for the ultrasound frequency in use, and the beamformed region (and/or the region of a displayed image) may be limited to the free depth range. By displaying only an image of the free depth region, any artifacts or other negative effects from overlapping echoes caused by transmitting overlapping pings may be avoided.

This technique may be used for performing very high frame-rate imaging of a narrow region within a target medium. A process for performing this technique may include the steps of defining a shallow edge and a deep edge of a free depth region (as described above), identifying echo data samples corresponding to the free depth region, beamforming the identified samples to form a high frame-rate set of images of the free depth region (or a sub-region within the free depth region), and displaying the images of the free depth region. In this way, imaging frame rates of 10,000 frames per second or more may be achieved, depending on the number of pings that are combined to form each frame (e.g., as described in the image layer combining section herein).

In various embodiments, one or more other methods of distinguishing echoes of one ping from echoes of another ping may also be used (alone or in combination with the methods above). Such other methods may include "coded excitation" techniques in which each "ping" has a uniquely recognizable waveform shape. Such other methods may include transmitting a first ping at a first frequency and transmitting a second immediately subsequent ping at a second, different, frequency. Echoes of the first ping may then be distinguished from echoes of the second ping based on the frequency of ultrasound signals received.

Identifying & Monitoring Fingerprints in Echo Data

In some embodiments, the step of identifying each fingerprint in the un-beamformed receive echo data 408 in FIG. 1 may comprise identifying one or more peaks of the transmitted tracking ping in a single reflector within the fingerprint point region. As described above, the tracking pings may be transmitted with a waveform shape having a short peak, as close to a sharp point as possible.

In some embodiments, the step of identifying each fingerprint in the un-beamformed receive echo data 408 in FIG. 1 may comprise identifying the fingerprint by identifying a pattern of data samples representing the fingerprint. In some cases, identifying the fingerprint data sample pattern may comprise first summing data samples for two or more elements and/or otherwise transforming the data. In some cases, identifying one or more fingerprint data strings may comprise identifying an approximate match of a string. An approximate match may be determined based on a Levenshtein distance (or other string metric) with a value below a pre-determined threshold (i.e., a fingerprint data string may be detected if a string within an expected range gate has is within a predetermined Levenshtein distance of a previously-identified fingerprint).

In other embodiments, motion detection may be performed by monitoring a position of a beamformed fingerprint within an imaged region as described below with reference to motion tracking processes.

In various embodiments, the step of monitoring a position of each fingerprint point within the un-beamformed echo data 410 may comprise monitoring digital samples within a range gate surrounding each selected fingerprint point. The position in time of the detected fingerprint may then be monitored in echo data (or in analog echo signals) for each successive tracking ping. If the fingerprint is seen to shift in time (or in sample position for a series of digital samples), then such a shift may be indicative of movement of the fingerprint point relative to the probe. Monitoring multiple points (e.g., at least three non-collinear points) from the vantage point of multiple receive elements may beneficially allow for the detection of motion in any of six degrees of motion.

Echoes of reflectors in each fingerprint point may be received by all receive elements of the probe. Therefore, if each receive element is joined to a separate receive channel such that digitized echoes received by each receive element may be digitally stored, then the position-in-time of the fingerprint from within a fiducial region may be monitored independently from the vantage point of each receive element. Therefore, each receive element may have an independent perspective of the position-in-time of the reflection fingerprint. Because the fingerprint and the fiducial region will likely be a different distance to each receive element, the range of digital samples defining the range gate to be monitored may typically be different for each element. Thus, a table of range gates may be created to define a range gate to be monitored for each receive element channel.

The size of a range gate to be monitored may be measured in time, in number of samples, or by any other suitable metric. The size of a range gate to be monitored may be as small as possible (so as to limit required processing time) while being as large as needed to detect an expected range of movement that may occur between tracking pings.

Detecting Fingerprint Position Shift

In various embodiments, the step of detecting a shift in position of at least one of the fiducial regions within the un-beamformed echo data 412 may comprise determining that a detected shift in the position-in-time of a fingerprint exceeds a threshold shift. For example, in various embodiments, the size of a shift in the position of a fingerprint that is interpreted as representing motion may vary depending on the degree of confidence desired, among other factors.

In some embodiments, the step of detecting a shift in position of at least one of the fiducial regions within the un-beamformed echo data 412 may comprise combining results from multiple receive elements into a single indication of "motion" or "no motion." If each receive element provides an independent indication of whether or not motion has been detected, then in some embodiments motion may be indicated if data from at least X receive elements indicate that movement of at least one fingerprint point has occurred. "X" may be any number from one element to all available receive elements, depending on the degree of confidence desired for a particular application. For example, in some embodiments a binary indication of motion may be determined for each element for the echoes of each transmitted tracking ping. If a value of 1 indicates movement, and a value of 0 indicates no movement, then the results for all elements may be summed, and a threshold total value may be established to evaluate the collective result to determine whether or not motion has occurred. In other embodiments, the results from all elements may be averaged, and a threshold average may be established to determine whether or not motion has occurred. In further embodiments, other aggregation algorithms may be used.

In other embodiments, receive elements used to detect motion may be spaced from one another across a probe. In one example, three or more elements spaced from one another by a distance of at least X may be polled to detect a changing position of a fingerprint. The value of X may depend on the size of the probe, and in some embodiments may be as great a distance as possible. In some examples, X may be at least 1 cm, at least 2 cm, at least 3 cm, at least 4 cm, at least 5 cm, at least 6 cm, at least 7 cm, or more. In some cases, groups of two, three or more receive elements at each of three locations spaced around the probe may be used. In such cases, the steps of monitoring the position of the fingerprint points (410) and detecting a shift in the position of a fingerprint point may comprise monitoring echo data corresponding to those selected receive elements.

Indicating Motion

In various embodiments, the step of producing a signal indicating that motion has occurred 414 may comprise providing a digital or analog signal from a motion detection block to a motion tracking block of an imaging system. In some embodiments, the step of producing a signal indicating that motion has occurred 414 may comprise providing an indication to a human operator that motion has occurred. For example, an indication to a human operator may comprise illuminating a light, turning off a light, flashing a light, displaying a message on a display screen, generating a sound, or any other indication. In some embodiments, the step of producing a signal indicating that motion has occurred 414 may comprise sending a signal stopping operation of a device such as a robotic surgery component such as a laser, an energy source, a mechanical cutter, or other device.

In some embodiments, in response to an indication that motion has occurred, a data recording process may be initiated during which raw echo data is stored in a non-volatile memory device for all tracking pings transmitted from a pre-determined time before the detection of motion until a pre-determined time after the detection of motion. For example, the system may include a circular buffer and instructions to store all ping and echo data for a period of time (or until a user stops recording of data) when motion is detected.

Tracking Motion of Fiducial Regions

Figure 2:
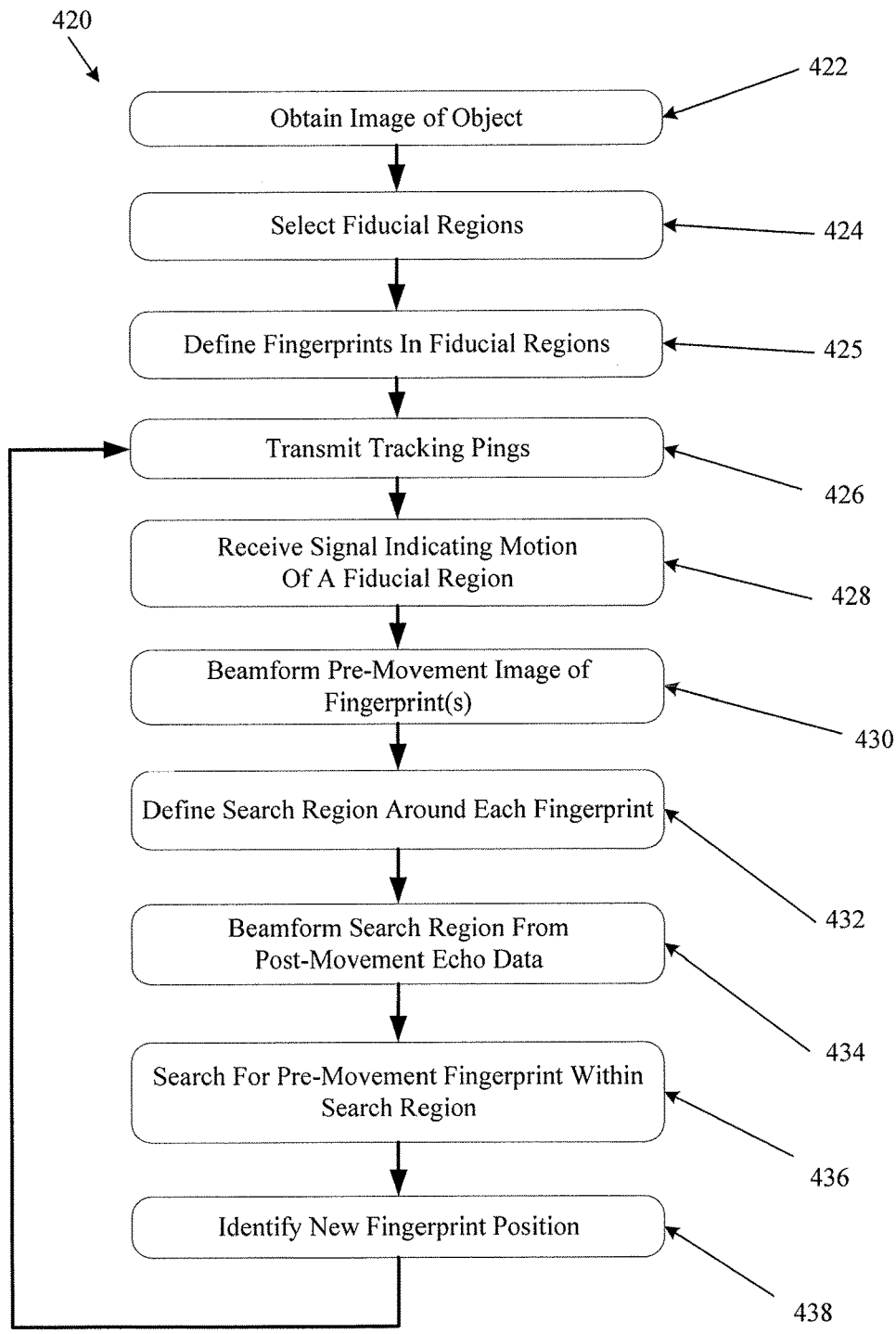
FIG. 2 is a process flow diagram illustrating a process for tracking motion in an object using an ultrasound system.

The process flow diagram of FIG. 2 illustrates an example of a motion tracking process 420 comprising the steps of: obtaining an image of an object to be tracked 422 within a medium, selecting a plurality of fiducial regions on or in the object to be tracked 424, defining fingerprints in the fiducial regions 425, transmitting a series of tracking pings into the medium 426; receiving a signal indicating that motion has occurred 428, beamforming a pre-movement image of at least one fingerprint point 430, defining a search region surrounding the fingerprint point 432, beamforming an image of the search region using post-movement echo data 434, searching the search region of the post-movement image for the fingerprint pattern identified in the pre-movement image 436, and identifying a new position of the fingerprint point(s) 438. In some embodiments, the new position may be communicated to an external device such as a robotic arm, a tracking system monitoring a position of the ultrasound probe, or any other electronic or electromechanical system. In some embodiments, after identifying a new position of the fingerprint point(s), the process 420 may return to block 426 to continue tracking the position of the fingerprint points from their new positions.

In various embodiments, the steps of obtaining an image of an object to be tracked 422 within a medium, selecting a plurality of fiducial regions on or in the object to be tracked 424, defining fingerprints within the fiducial regions 425, and transmitting a series of tracking pings into the medium 426 may be substantially the same as the steps described above with reference to FIG. 1.

In some embodiments, a fingerprint may be sized to be smaller than the lateral and/or axial resolution limits of the imaging system. In such embodiments, the fingerprint point may represent a pattern of transmitted wavefronts at a particular point within or on the object rather than actual visible features of the object. In such embodiments, tracking of the fingerprint point may be improved by an imaging system that produces wavefronts that intersect at significant angles to one another at the object to be tracked. For example, if wavefronts intersect at approximately 90 degrees to one another at the fingerprint point, a beam-formed representation of the pattern of intersecting waveforms may be substantially unique within at least the local region of the insonified field compared with other similarly situated regions. In some embodiments, such a representation may comprise a cross-hatched pattern of intersecting lines when displayed (whether or not such points are actually displayed).

Figure 4A:
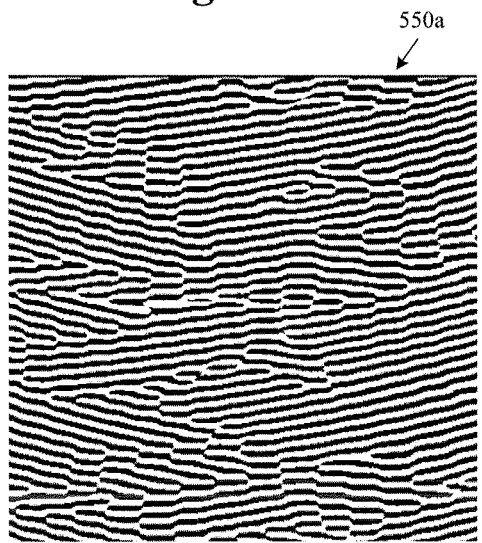
FIG. 4A and FIG. 4B illustrate some cross-hatched fingerprint patterns derived from data collected using a multiple aperture ping-based ultrasound imaging system.
Figure 4B:
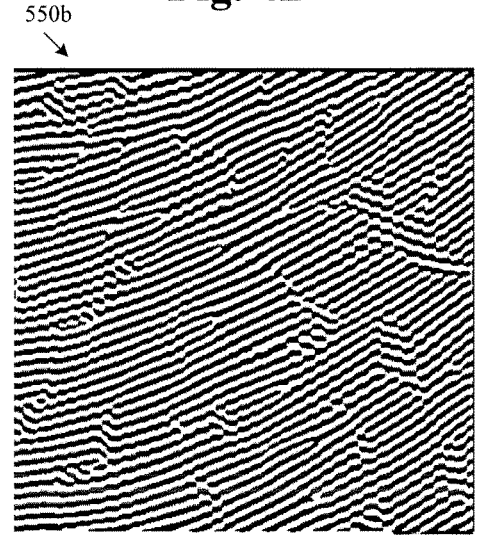

FIG. 4A and FIG. 4B illustrate some example cross-hatched fingerprint patterns 550a, 550b derived from data collected using a multiple aperture ping-based ultrasound imaging system as described herein. The patterns 550a, 550b are shown in exaggerated black-and-white in order to highlight the pattern. In an imaging system, patterns may be produced in grayscale and may therefore provide more nuanced detail. Nonetheless, the illustrations of FIG. 4A and FIG. 4B are sufficient to give an idea of the types of patterns being described.

The patterns of FIG. 4A and FIG. 4B exhibit cross-hatching resulting from the interaction of waveforms at a fingerprint point with an area that is a small fraction of a resolving ability of the imaging system. The patterns do not necessarily represent any actual physical structure within the imaged medium, but variations in the imaged medium between the probe and a selected point may affect the pattern of waveforms that appear at the selected point.

As described elsewhere herein, the pattern of intersecting diagonals may be produced by using an ultrasound probe that is wide enough that elements located furthest from one another may provide significantly different view angles of a selected fiducial point. Summing those viewpoints into a single image may form crossing-diagonal patterns such as those shown.

In some cases, a probe with a multiple physically separated receive arrays (which may or may not be angled towards one another) may achieve such a unique waveform intersection pattern. In other cases, a probe with a receive array that is wide enough that elements closest to the extents of the array have a substantial look angle (e.g., and angle significantly greater than zero degrees to a vertical line, up to about 45 degrees or more) at the fingerprint points may provide a desirable unique waveform intersection pattern. Further examples of probe configurations are described below.

In some embodiments, it may be desirable to select at least three non-collinear points as fingerprint points. Selecting non-collinear points may increase the confidence that any motion in any direction will be detected. In some embodiments, it may also be desirable to select points that are separated from one another by a sufficient distance that motion may be adequately detected and/or tracked in three dimensions.

In various embodiments, the step of receiving a signal indicating that motion has occurred 428 may comprise receiving a signal resulting from a motion detection process described above. In other embodiments, receiving a signal indicating that motion has occurred 428 may comprise receiving a signal from a different system based on a different motion detection process. In various embodiments, the signal may indicate the number and/or identity of fingerprint points for which motion has been detected.

In various embodiments, the step of beamforming a pre-movement image of at least one fingerprint point 430 may comprise beamforming only the regions of the imaged object defined as fingerprint points, or only the region defined as the fingerprint point for which motion is indicated. The fingerprint region may contain a unique pattern that is human-visible, machine-readable, or both. The unique pattern may define a fingerprint that may be tracked within a larger region in order to track motion of the fingerprint point. In other words, the step of beamforming a pre-movement image of at least one fingerprint point 430 may comprise not beamforming any regions of the image other than those defined as fingerprint points.

In some embodiments, the step of beamforming a pre-movement image 430 may comprise beamforming an area larger than the defined fingerprint point (e.g., the entire fiducial region defined at block 424), and a sub-section of the beamformed area may be selected as the fingerprint pattern. In some embodiments, the sub-section may correspond to a region defined as the fingerprint point. In some embodiments, the area beamformed as a pre-movement image may be an area defined as a search region as described below.

Because software-based beamforming may involve some processing time, minimizing the beamforming to the smallest area possible may substantially reduce the processing time needed to track movement of the object. In some embodiments, search regions and/or fingerprint point regions of each of one, two, three, or more fingerprint points may be beamformed simultaneously in parallel processes.

Data samples corresponding to fingerprint points and to search areas surrounding fingerprint points may be identified based on known positions of the transmitting and receiving transducer elements, a speed-of-sound of the transmitted and received ultrasound signals in the imaged medium, and the timing of transmitted and received signals. Therefore, in some embodiments, data samples corresponding to fingerprints may be identified at the time that fingerprint points are defined. Based on this information, data samples corresponding to regions to be beamformed may be efficiently located, retrieved and used to form images or evaluated directly to detect patterns.

In various embodiments, the step of beamforming a pre-movement image 430 may comprise beamforming the echoes received from the ping immediately before the ping during which motion was detected. In other words, assuming tracking pings may be numbered sequentially from $P_0$ through $P_n$, if motion was detected based on a shift of a fingerprint in the echoes of ping number $P_7$ compared to the echoes of ping number $P_6$, then the pre-movement image of each test region or all regions surrounding each fingerprint point may be generated using the echoes of any of the pings number P6, P5, or earlier pings (e.g., any of P0 through P6). In some embodiments, echoes of previously-transmitted pings may be stored in a circular buffer to facilitate analysis of echoes received prior to detection of motion.

In some embodiments, the size of the pre-movement beamformed region around each fingerprint point may be exactly the size of a defined fingerprint point. In other embodiments, the beamformed region around each fingerprint point may be slightly or substantially larger than the fingerprint point, such as 10% larger, 20% larger, 30% larger, 50% larger, 1.5 times, 2 times, 3 times, or more, larger than the fingerprint point.

In various embodiments, the step of defining a search region surrounding each fingerprint point 432 may comprise defining an area within which the fingerprint may have moved in the time between the pre-movement image and the post-movement image to be evaluated. For example, if the fingerprint point may have feasibly moved by 100% of the width of the fingerprint point in any direction, then the search region may be an area that is at least as large as the area into which the fingerprint point may have moved.

For a square or rectangular point, the search area may comprise nine squares or rectangles with the original fingerprint point in the center position. This may allow for tracking the fingerprint's movement only within one multiple of its dimensions (or ~1.4 times along the diagonal directions). In other embodiments, the search area may be defined as a multiple of the size of the fingerprint area, where the multiple is at least large enough that a maximum expected motion between transmitted pings may still be within the search area. For example, the search area may be defined as five times the dimensions of the fingerprint point, thereby allowing for the fingerprint to have moved up to twice its dimension from its previous position. In other embodiments, the search area may be defined as 7 times, 9 times, or 11 times, the dimensions of the fingerprint point, or larger. Thus, the size of the search region may be based on the size of the fingerprint, the ping repetition rate, and/or the expected degree of motion that may occur between consecutive pings.

In some embodiments, the step of defining a search region surrounding each fingerprint point 432 may comprise defining the search region to be the same size as the fiducial region defined in block 424.

Searching for the pre-movement fingerprint pattern within the search region 436 may comprise comparing the fingerprint pattern from the pre-movement image to a plurality of test regions in the post-movement image as potential new positions for the fingerprint point. Defining test regions may comprise defining regions shifted by, for example, one unit (where a "unit" is defined as a region the same shape and dimensions of the fingerprint) from a defined fingerprint point location. For example, four test regions may be defined by defining areas the same size as but shifted from the beamformed pre-movement image of a fingerprint point by one unit in each vertical and horizontal direction (e.g., shifted left by one unit, shifted right by one unit, shifted up by one unit, and shifted down by one unit). Another four test regions may be defined by shifting diagonally from the beamformed pre-movement image of a fingerprint point, such as shifting up one unit and right one unit; shifting up one unit and left one unit;

shifting down one unit and right one unit, and shifting down one unit and left one unit.

In various embodiments, the step of beamforming images of search regions using post-movement echo data 434 may comprise identifying echoes of one or more tracking pings transmitted after motion occurred. For example, if motion was detected based on a shift between ping number P6 and ping number P7, then echoes of P7 or later pings may be considered to be post-movement echo data. In some embodiments, the echoes of two or more post-movement pings may be combined (e.g., coherently or incoherently summed or averaged). In some embodiments, beamforming pre-movement and/or post-movement images may include the use of ping-based multiple aperture imaging techniques and image layer combining techniques to combine images (coherently and/or incoherently) obtained by multiple individual transducer elements which may be grouped into one or more receive apertures as described elsewhere in this disclosure.

In various embodiments, the step of beamforming images of search regions using post-movement echo data 434 may comprise beamforming only those portions of the region of interest defined as test regions. In other words, the step of beamforming images of search regions using post-movement echo data 434 may comprise not beamforming any portions of the region of interest that are not defined as a test region. In this way, the processing time needed for performing beamforming calculations may be dramatically reduced relative to beamforming an entire region of interest or an entire contiguous image.

In various embodiments, the step of searching for the pre-movement fingerprint pattern in the post-movement image of the search region 436 may comprise the use of cross-correlation techniques in which each unit of each test region is compared with each unit of the pre-movement image to identify the highest correlation between a test-region image and the pre-movement image. The test region that is most highly correlated with the pre-movement image of the fingerprint point may be selected as the new fingerprint point position 438.

In some embodiments, the step of searching for the pre-movement fingerprint pattern in the post-movement image of the search region 436 may comprise subtracting each unit of the pre-movement image from each corresponding unit of each test region to obtain one difference image corresponding to each subtraction. The difference image with the lowest value may be identified as the closest match with the pre-movement image. As a result, the test image region corresponding to the lowest value difference image may be identified as the new position for the fingerprint point 438. In other embodiments, any other motion estimation or image search process may be used to identify a new position of the fingerprint pattern within a post-movement search region image. For example, other statistical measures (e.g., median, standard deviations, etc.) of a difference image may be used to select a test region most closely matching the fingerprint point.

In some embodiments, a new position of one or more fingerprint points and/or a new position of the object may be communicated to an external device, such as a robotic surgery control system, a human interface such as a display or an audible notification, or to another control system.

In some embodiments, a motion detection process and a motion tracking process may be performed simultaneously in parallel. In other embodiments, a motion tracking process may be initiated only after a motion detection process has detected that motion has occurred.

In some embodiments, the step of receiving a signal indicating that motion has occurred 428 may be omitted, and the entire process 420 of FIG. 2 may be run continuously, returning to block 426 after identifying a new position of one or more fingerprint points at block 438. In some such embodiments, the process 420 of FIG. 2 may be used for both motion detection and motion tracking. For example, if the search process of block 436 determines that the fingerprint point is in the same position in the "post-movement" image that it was in the "pre-movement" image, then the process may determine that no motion has occurred. On the other hand, if the search process of block 436 determines that the fingerprint point is not in the same position in the "post-movement" image that it was in the "pre-movement" image, then the process may simultaneously determine that motion has occurred and track the new position of the fingerprint point(s).

In such a case, the "pre-movement" image may simply be a first image obtained at a first time, and a "post-movement image" may be a second image obtained at a second, later time. The frame rate at which such images are obtained may be selected based on a desired motion update rate. Due to the time required to beamform the search regions, such embodiments may be slightly slower at motion detection than using the motion detection process based on un-beamformed data described above with reference to FIG. 1. However, such a cost may small in view of the extremely high frame rates possible using ping-based imaging techniques as described elsewhere herein.

In some embodiments, normal imaging pings (e.g., two dimensional pings or three-dimensional pings) may be transmitted from one or more transmit elements of a probe and echoes may be collected to obtain fully beamformed two-dimensional images, three-dimensional volumes, or two-dimensional images extracted from three-dimensional volumetric data substantially simultaneously with performing a motion detection and/or motion tracking process. In some embodiments, imaging pings may be interleaved or alternated with tracking pings. In other embodiments, tracking may be suspended while imaging pings are transmitted and imaging echo data is collected.

In various embodiments, any of the probes shown and described herein may be used for performing motion detection and/or motion tracking by one or more of the processes described herein.

Configurations of Imaging Probes for Motion Detection and Motion Tracking

Figure 5:
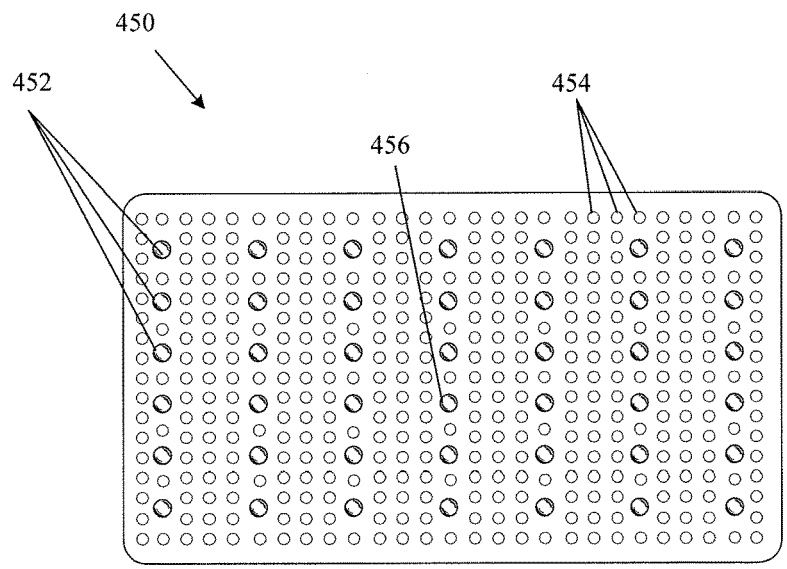
FIG. 5 is a schematic illustration of an example imaging probe array having a plurality of transmitting transducer elements and a plurality of circular receiving transducer elements.

FIG. 5 illustrates an example embodiment of an ultrasound probe 450 configured for three-dimensional ping-based multiple aperture imaging as described above. The probe 450 of FIG. 5 may comprise a plurality of apparent-point-source transmit elements 452 (or other dedicated transmit transducer elements), and a plurality of receive elements 454.

When used for motion tracking and/or motion detection, one or more of the transmit elements 452 may be designated as a tracking ping transmitter element (e.g., element 456 or any other single transmit element 452) from which tracking pings may be transmitted during a motion tracking and/or motion detection process. In various embodiments, all of the receive elements 454 of the probe 450 or a sub-set of all of the receive elements 454 of the probe 450 may be used as receive elements during a motion tracking and/or motion detection process. In some embodiments, raw echo data may be received and stored separately for each and every receive element 454 of the probe 450. In some embodiments, analysis may be limited to echo data from only a subset of all of the receive elements 454 of the probe 450. In other embodiments, analysis may be performed using echo data from all of the receive elements 454 of the probe 450.

An example of performing the motion detection process 400 of FIG. 1 using the probe 450 of FIG. 5 will now be described. The probe 450 may be used to obtain three-dimensional volumetric images of the medium and the object to be tracked 402 using any of the imaging systems and methods described herein. Alternatively, the probe 450 and an imaging system (e.g., as described elsewhere herein) may be used to obtain one or more images of one or more two-dimensional planes from within the three dimensional volume of the medium. Fingerprint points may be selected 404 from one or more two-dimensional images, from a three-dimensional volumetric rendering, or using an automated software agent.

In some embodiments, transmission of tracking pings 406 in the process 400, may comprise designating a single transmit element, such as element 456 (or any other transmit element), as a tracking ping transmitter. Transmitting tracking pings from only a single transmitter may simplify the process of detecting motion, because the position-in-time of the fingerprint point reflectors relative to the transmit element need only be determined once. Nonetheless, in some embodiments, tracking pings may be transmitted from two or more transmit elements.

Echo data received by each of the receive elements 454 may be separately stored as described above. Data representing echoes of each tracking ping may be stored in a short-term or long-term memory device, and may be evaluated to identify one or more reflectors within each fingerprint point according to process step 408, such as by identifying a fingerprint in the data. The position of a fingerprint may be monitored by determining which sample number (or sample numbers) represents the fingerprint. The sample number representing the fingerprint each fiducial region may be referred to as the stationary sample. If the fingerprint is detected in a different sample position before or after the stationary sample, then a determination may be made that the fingerprint point (and therefore the fiducial region) has moved. In some embodiments, movement may be indicated if a fingerprint detected as moving by only a single sample position from the stationary sample. In other embodiments, movement may be indicated if a fingerprint is detected as moving by two, three, four, five, six, seven, eight, nine, ten, or more samples from the stationary sample. In some cases, a size of a sample shift indicating movement may be a function of digital sampling rate.

In some embodiments, the stationary position of a fingerprint may be defined in terms of time rather than sample position. For example, in some embodiments the position of a fingerprint may be monitored by evaluating an analog echo signal for each receive element. This may be particularly beneficial if the fingerprint contains a recognizable peak or pattern of peaks. Movement of the fingerprint by a pre-determined number of nanoseconds (or other value of time) may be indicative of movement. In some embodiments, because the probe 450 may collect three-dimensional volumetric data from the echoes of each ping, monitoring a position of a fingerprint 410 may comprise monitoring the fingerprint's position in three dimensions at an update rate which may be as high as the rate at which tracking pings are transmitted. As discussed above, in some embodiments, tracking pings may be transmitted at a rate of 1,000 pings per second, 2000 pings per second, 3,000 pings per second, 5,000 pings per second, 10,000 pings per second or more.

When using the probe 450 of FIG. 5 to perform a motion tracking process such as the process 420 of FIG. 2, any or all of the steps of beamforming a pre-movement image 430, defining test regions 432, beamforming the test regions 434, searching for the pre-movement fingerprint in the search region 436, and identifying a new fingerprint position may be performed using a digital or graphical representation of three-dimensional volumetric data. For example, the pre-movement image may comprise a three-dimensional volume of voxels. Similarly, the test regions may comprise three-dimensional volumes of voxels, and comparing the pre-movement image with test region images 436 may comprise comparing voxels of the pre-movement volume with each test region volume. In some embodiments, the comparison may comprise performing a cross-correlation of voxels to determine which of the test-region volumes is most closely matched with the pre-movement volume. In some embodiments, the comparison may comprise subtracting voxels of the pre-movement image from voxels of each of the test regions to obtain a plurality of difference volumes. Identifying a new fingerprint point position may comprise defining a new three-dimensional volume representing a new position for one or more fingerprint points.

In other embodiments, one, two, three or more two-dimensional slices through the fiducial regions may be calculated from a received three dimensional volumetric representation of the imaged region (as described elsewhere herein), and two-dimensional representations of each search region may be beamformed in the defined plane(s). For example, in one embodiment, a different two-dimensional plane may be defined for each fiducial region, or for each combination of fiducial region and receive element (or receive aperture). Alternatively, a single plane intersecting all three (or more) fiducial regions may be defined as a plane in which search regions may be beamformed.

Figure 6:
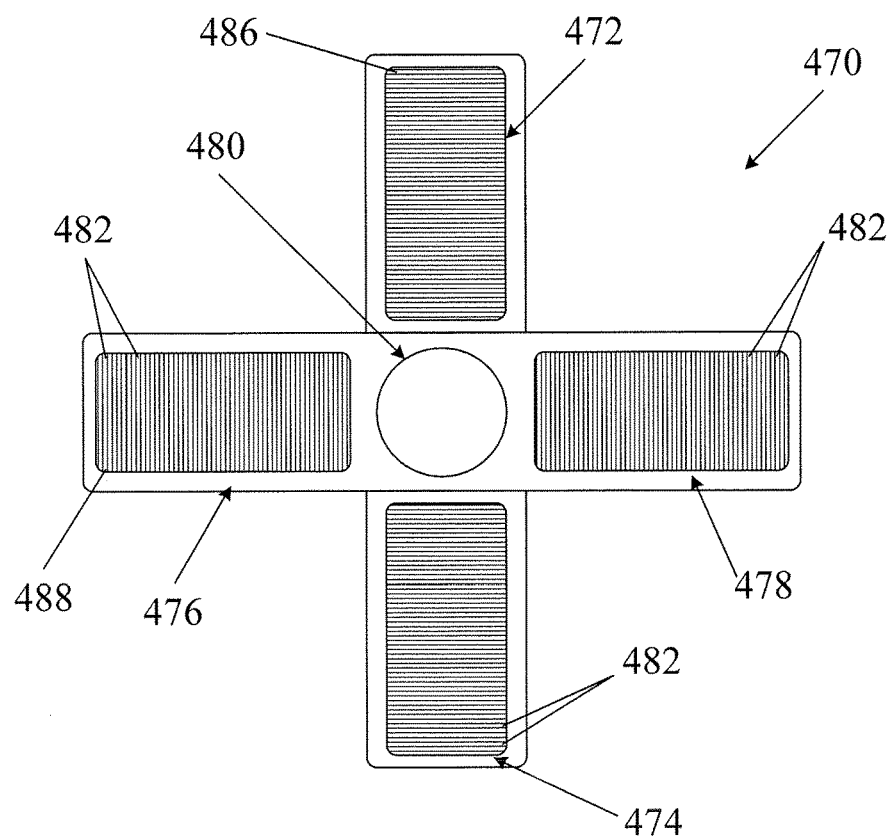
FIG. 6 is a diagram illustrating a cross-shaped probe suited for use in a motion detection and/or motion tracking process.

FIG. 6 illustrates an example embodiment of an ultrasound probe 470 configured for performing an example motion detection and motion tracking process by evaluating echo data in two substantially planar image regions. The probe 470 may comprise a plurality of linear transducer arrays 472, 474, 476, 478 (also referred to as 1D arrays) of and one or more transmit elements 480.

Each array 472, 474, 476, 478 may comprise a plurality of linear transducer elements 482 which may be focused into a two-dimensional region (which may also be referred to as an "image plane" of the array) by a lensing material as is well understood in the art of ultrasound transducers. Due to the nature of focused linear arrays, the so-called "two-dimensional focused region" of each array may actually have some thickness in a dimension normal to the image plane. The thickness of the two-dimensional focused region may vary by depth into the medium from the array based on the shape of a lensing material interposed between the elements 482 and the medium to be imaged.

A first pair 472, 474 of the arrays may be arranged such that the two-dimensional focused region of a first array 472 is aligned with the two-dimensional focused region of a second array 474. The overlapping two-dimensional focused region of the first and second arrays may be referred to as a first common image plane.

Similarly, a second pair 476, 478 of the arrays may be arranged such that the two-dimensional focused region of a third array 476 is aligned with the two-dimensional focused region of a fourth array 478. The overlapping two-dimensional focused region of the third and fourth arrays may be referred to as a second common image plane.

The first common image plane of the first pair of arrays 472, 474 may intersect the second common image plane of the second pair of arrays 476, 478 at right angles or at any other angle as desired. In various embodiments, one, two, three, four or more arrays may be aligned with each common image plane. The first and second common image planes may have unequal numbers of arrays or elements. In some embodiments, additional arrays may be provided and focused on a third (or additional) image plane that intersects one or both of the first and second common image planes.

In various embodiments, some of the one-dimensional elements may be designated as transmit elements and others may be designated as receive elements. In other embodiments, all one-dimensional elements 482 may be switchable between transmit and receive functions.

When used for motion tracking and/or motion detection, one or more of the one-dimensional elements 482 may be designated as a tracking ping transmitter element from which tracking pings may be transmitted during a motion tracking and/or motion detection process. In other embodiments, a transmit element 480 may be used as a tracking ping transmit element.

In various embodiments, all of the one-dimensional elements 482 of the probe 470 or a sub-set of all of the one-dimensional elements 482 of the probe 470 may be used as receive elements during a motion tracking process 400 and/or motion detection process 420. In some embodiments, raw echo data may be received and stored separately for each and every receive element of the probe 470. In some embodiments, analysis may be limited to echo data from only a subset of all of the receive elements 482 of the probe 470. In other embodiments, analysis may be performed using echo data from all of the receive elements 482 of the probe 470.

An example of performing the motion detection process 400 of FIG. 1 using the probe 470 of FIG. 6 will now be described. The probe 470 may be used to obtain two intersecting two-dimensional images of the medium and the object to be tracked 402 using any of the imaging systems and methods described herein. For example, a first two-dimensional image of the medium and the object may be obtained using the first pair of arrays 472, 474 focused on the first common image plane. One or more fingerprint points may be selected 404 from the first image by a human operator, or by an automated software agent.

A second two-dimensional image of the medium and the object may be obtained using the second pair of arrays 476, 478 focused on the second common image plane. One or more fingerprint points may be selected 404 from the first image by a human operator, or by an automated software agent. The first and second two-dimensional images may be obtained using any suitable imaging process, which may include a two-dimensional ping-based multiple aperture imaging process as described above.

In some embodiments, the first image and/or the second image may include a visual indication of an overlapping region of the two images. Such an indication may be provided in the form of colored lines, a color-shaded region, a region of higher or lower brightness, or otherwise.

In some embodiments, transmission of tracking pings 406 in the process 400, may comprise designating a single transmit element from each common image plane, such as element 486 of the first array 472 and element 488 of the third array 476 (or any other transmit element of any of the arrays), as a tracking ping transmitter. Transmitting tracking pings from only a single transmitter may simplify the process of detecting motion, because the position-in-time of the fingerprint point reflectors relative to the transmit element need only be determined once. Nonetheless, in some embodiments, tracking pings may be transmitted from two or more transmit elements.

Tracking pings may alternatively be transmitted from the transmit element 480. The transmit element 480 may transmit three-dimensional wavefronts, each of which may be received by receive elements of the arrays 472, 474, 476, 478 focused on a single image plane as described above. In this way, a single transmit element may transmit tracking pings, the echoes of which may be received separately in each of the two common image planes.

When using the probe 470 of FIG. 6 to perform a motion tracking process such as the process 420 of FIG. 2, any or all of the steps of beamforming a pre-movement image 430, defining test regions 432, beamforming the test regions 434, comparing test region images with the pre-movement image 436, and identifying a new fingerprint point position 438 may be performed using two-dimensional images of at least portions of each of the first common image plane and the second common image plane. For example, the pre-movement image may comprise a graphical or digital representation of a two-dimensional image of a fingerprint point. Similarly, the test regions may comprise two-dimensional regions of units within one or both of the common image planes. Comparing the pre-movement image with test region images 436 may comprise comparing units of the pre-movement two-dimensional image with units of two-dimensional images of each test region. In some embodiments, the comparison may comprise performing a cross-correlation of units to determine which of the test-region images is most closely matched with the pre-movement image. In some embodiments, the comparison may comprise subtracting units of the pre-movement image from units of each of the test regions to obtain a plurality of difference images. Identifying a new fingerprint point position may comprise defining a new two-dimensional image representing a new position for one or more fingerprint point.

In other embodiments, any other ultrasound probe capable of being used to perform the methods described herein may also be used. For example, probes configured for two-dimensional scanline-based or ping-based imaging may also be used. In some embodiments, two or more probes may be used in tandem for a motion tracking and/or motion detection process.

Evaluating Material Elasticity

In some embodiments, the techniques described herein may be used to evaluate the elasticity of an imaged material. Techniques known as "elastography" may generally involve mechanically distorting a material by transmitting a shear-wave inducing pulse into the material and monitoring the speed at which the shear wave propagates in the material. The shear wave propagation speed may then be used to determine material stiffness and the modulus of elasticity of the imaged material.

The systems and methods described herein may be used to measure the speed of propagation of a shear wave. In one example, a plurality of fingerprint points (e.g., four, five, ten, twenty or more points) may be defined, a shear-wave-initiating pulse may be transmitted, and the position of each of the defined points may be tracked as described herein. The resulting position and time information may then be evaluated to determine the shear wave propagation speed.

In some cases, echo data may be collected and stored while the shear wave propagates. The stored echo data may then be analyzed in multiple trials, defining a different set of fingerprint points during each trial. The results of the multiple trials may then be aggregated to provide a more complete representation of motion of various portions of the imaged medium. Trials may be evaluated in parallel (e.g., simultaneously or contemporaneously with one another), or in series (e.g., one after the other).

In other embodiments, the elastic modulus of an imaged material may be measured directly using motion tracking methods described herein. Because the motion tracking methods described herein may provide information about movement of very small points at very high speeds, the motion tracking methods may be used to detect a displacement (or strain) of any number of points within an imaged object or material. Elastic modulus is equal to an applied stress (force per unit area) divided by a resulting strain (displacement). Therefore, a modulus of elasticity may be determined by applying a known stress to an object, tissue, or material, and then using the motion tracking techniques described herein to measure a resulting strain. Strain may be measured at a plurality of points, and the results may be averaged or otherwise combined (e.g., using a finite element method, in some cases) to obtain an overall elastic modulus or a plurality of region-specific elastic moduli.

Evaluating Fluid Flow

The systems and methods described herein may also be used to evaluate fluid flow in a conduit or vessel containing a flowing fluid. For example, multiple points (e.g., 2, 3, 4, 5, 10, 20, or hundreds of points) may be identified within the conduit or vessel. The position of those points may then be monitored as described herein for as long as possible. Depending on the nature of the flow and/or the nature of the fluid, the pattern representing each fingerprint point may change as the fluid moves. Thus, the system may be configured to determine when a pattern representing a point has degraded too much to continue using the point. At that time, the system may then define a new point to replace the degraded point. In some cases, the new point may be defined at or near a last-known position of the degraded point. In other cases, the new point may be projected based on a position of the point during a previous two, three, or more pings. The position of the new point may then be tracked along with the other points.

In some cases, echo data may be collected and stored for a period of time while the fluid is flowing or otherwise moving. The stored echo data may then be analyzed in multiple trials, defining a different set of fingerprint points within the fluid during each trial. The results of the multiple trials may then be aggregated to provide a more complete representation of motion of various portions of the imaged fluid. Trials may be evaluated in parallel (e.g., simultaneously or contemporaneously with one another), or in series (e.g., one after the other).

Multiple Aperture Ultrasound Imaging System Components

Figure 7:
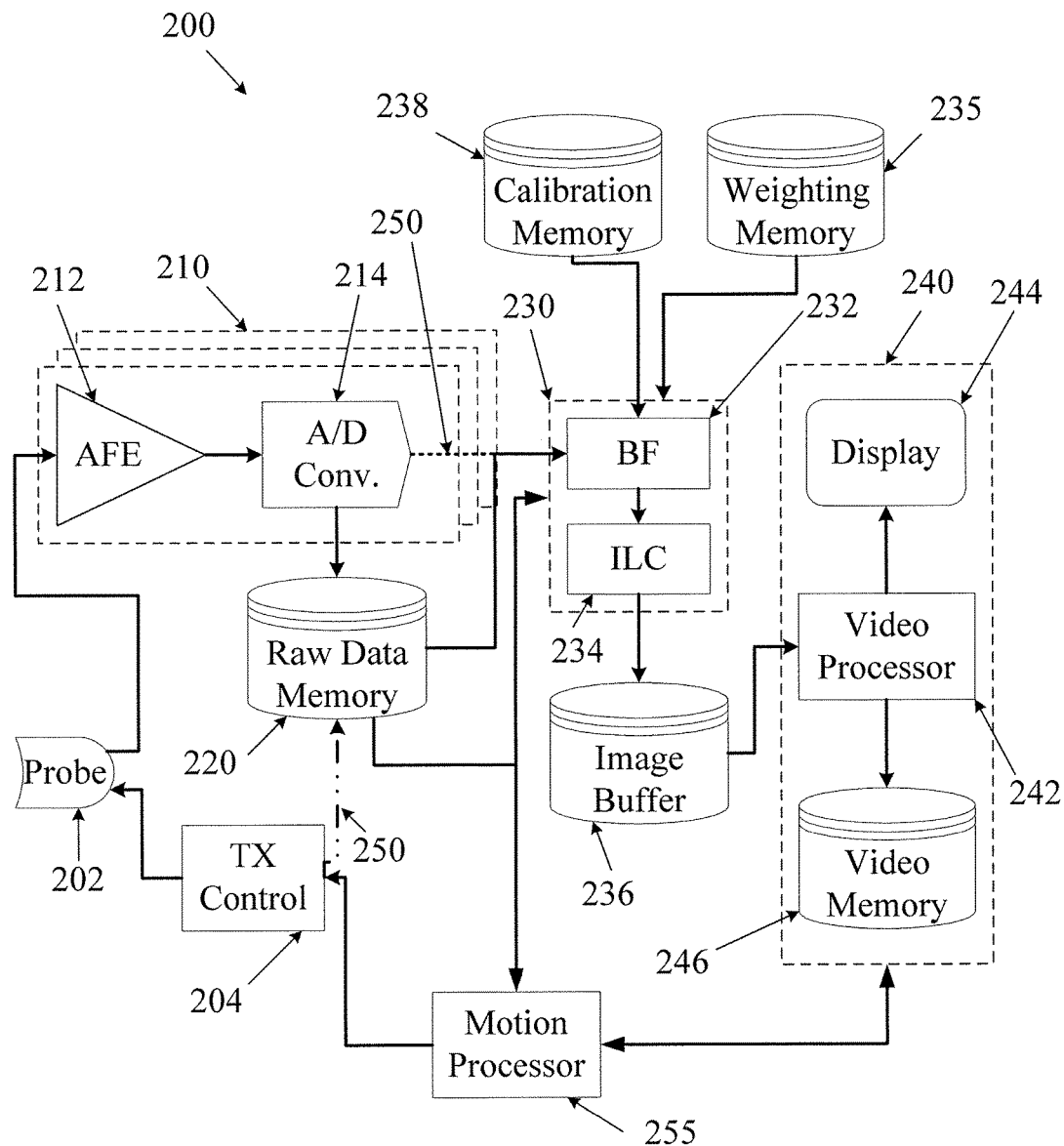
FIG. 7 is a schematic view illustrating an embodiment of a multiple aperture imaging system.

The block diagram of FIG. 7 illustrates components of an ultrasound imaging system 200 that may be used in combination with various embodiments of systems and methods as described herein. The system 200 of FIG. 7 may include several subsystems: a transmit control subsystem 204, a probe subsystem 202, a receive subsystem 210, an image generation subsystem 230, and a video subsystem 240. In various embodiments, the system 200 may also include one or more memory devices for containing various data for use during one or more ultrasound imaging steps. Such memory devices may include a raw echo data memory 220, a weighting factor memory 235, a calibration data memory 238, an image buffer 236 and/or a video memory 246. In various embodiments all data (including software and/or firmware code for executing any other process) may be stored on a single memory device. Alternatively, separate memory devices may be used for one or more data types.

The transmission of ultrasound signals from elements of the probe 202 may be controlled by a transmit control subsystem 204. In some embodiments, the transmit control subsystem 204 may include any combination of analog and digital components for controlling transducer elements of the probe 202 to transmit un-focused ultrasound pings at desired frequencies and intervals from selected transmit apertures according to a desired imaging algorithm. In some embodiments a transmit control system 204 may be configured to transmit ultrasound pings at a range of ultrasound frequencies. In some (though not all) embodiments, the transmit control subsystem may also be configured to control the probe in a phased array mode, transmitting focused (i.e., transmit beamformed) ultrasound scanline beams.

In some embodiments, a transmit control sub-system 204 may include a transmit signal definition module 206 and a transmit element control module 208. The transmit signal definition module 206 may include suitable combinations of hardware, firmware and/or software configured to define desired characteristics of a signal to be transmitted by an ultrasound probe. For example, the transmit signal definition module 206 may establish (e.g., based on user inputs or on pre-determined factors) characteristics of an ultrasound signal to be transmitted such as a pulse start time, pulse length (duration), ultrasound frequency, pulse power, pulse shape, pulse direction (if any), pulse amplitude, transmit aperture location, or any other characteristics.

The transmit element control module 208 may then take information about the desired transmit pulse and determine the corresponding electrical signals to be sent to the appropriate transducer elements in order to produce this signal. In various embodiments, the signal definition module 206 and the transmit element control module 208 may comprise separate electronic components, or may include portions of one or more common components.

Upon receiving echoes of transmitted signals from a region of interest, the probe elements may generate time-varying electrical signals corresponding to the received ultrasound vibrations. Signals representing the received echoes may be output from the probe 202 and sent to a receive subsystem 210. In some embodiments, the receive subsystem may include multiple channels, each of which may include an analog front-end device ("AFE") 212 and an analog-to-digital conversion device (ADC) 214. In some embodiments, each channel of the receive subsystem 210 may also include digital filters and data conditioners (not shown) after the ADC 214. In some embodiments, analog filters prior to the ADC 214 may also be provided. The output of each ADC 214 may be directed into a raw data memory device 220. In some embodiments, an independent channel of the receive subsystem 210 may be provided for each receive transducer element of the probe 202. In other embodiments, two or more transducer elements may share a common receive channel.

In some embodiments, an analog front-end device 212 (AFE) may perform certain filtering processes before passing the signal to an analog-to-digital conversion device 214 (ADC). The ADC 214 may be configured to convert received analog signals into a series of digital data points at some pre-determined sampling rate. Unlike most ultrasound systems, some embodiments of the ultrasound imaging system of FIG. 7 may then store digital data representing the timing, phase, magnitude and/or the frequency of ultrasound echo signals received by each individual receive element in a raw data memory device 220 before performing any further receive beamforming, filtering, image layer combining or other image processing.

In order to convert the captured digital samples into an image, the data may be retrieved from the raw data memory 220 by an image generation subsystem 230. As shown, the image generation subsystem 230 may include a beamforming block 232 and an image layer combining ("ILC") block 234. In some embodiments, a beamformer 232 may be in communication with a calibration memory 238 that contains probe calibration data. Probe calibration data may include information about the precise position, operational quality, and/or other information about individual probe transducer elements. The calibration memory 238 may be physically located within the probe, within the imaging system, or in location external to both the probe and the imaging system.

In some embodiments, after passing through the image generation block 230, image data may then be stored in an image buffer memory 236 which may store beamformed and (in some embodiments) layer-combined image frames. A video processor 242 within a video subsystem 240 may then retrieve image frames from the image buffer, and may process the images into a video stream that may be displayed on a video display 244 and/or stored in a video memory 246 as a digital video clip, e.g., as referred to in the art as a "cine loop".

In some embodiments, the AFE 212 may be configured to perform various amplification and filtering processes to a received analog signal before passing the analog signal to an analog-to-digital conversion device. For example, an AFE 212 may include amplifiers such as a low noise amplifier (LNA), a variable gain amplifier (VGA), a bandpass or lowpass/anti-aliasing filter, and/or other amplification or filtering devices. In some embodiments, an AFE device 212 may be configured to begin passing an analog signal to an ADC 214 upon receiving a trigger signal. In other embodiments, an AFE device can be "free running", continuously passing an analog signal to an ADC.

In some embodiments, each analog-to-digital converter 214 may generally include any device configured to sample a received analog signal at some consistent, predetermined sampling rate. For example, in some embodiments, an analog-to-digital converter may be configured to record digital samples of a time-varying analog signal at 25 MHz, which is 25 million samples per second or one sample every 40 nanoseconds. Thus, data sampled by an ADC may simply include a list of data points, each of which may correspond to a signal value at a particular instant. In some embodiments, an ADC 214 may be configured to begin digitally sampling an analog signal upon receiving a trigger signal. In other embodiments, an ADC device can be "free running", continuously sampling a received analog signal.

In some embodiments, the raw data memory device 220 may include any suitable volatile or non-volatile digital memory storage device. In some embodiments, the raw data memory 220 may also comprise communication electronics for transmitting raw digital ultrasound data to an external device over a wired or wireless network. In such cases, the transmitted raw echo data may be stored on the external device in any desired format. In other embodiments, the raw data memory 220 may include a combination of volatile memory, non-volatile memory and communication electronics.

In some embodiments, the raw data memory device 220 may comprise a temporary (volatile or non-volatile) memory section, and a long-term non-volatile memory section. In an example of such embodiments, the temporary memory may act as a buffer between the ADC 214 and the beamformer 232 in cases where the beamformer 232 may be unable to operate fast enough to accommodate data at the full rate from the ADC 214. In some embodiments, a long-term non-volatile memory device may be configured to receive data from a temporary memory device or directly from the ADC 214. Such a long-term memory device may be configured to store a quantity of raw echo data for subsequent processing, analysis or transmission to an external device.

In some embodiments, the beamforming block 232 and the image layer combining block 234 may each include any digital signal processing and/or computing components configured to perform the specified processes (e.g., as described below). For example, in various embodiments the beamforming 232 and image layer combining 234 may be performed by software running on a single GPU, on multiple GPUs, on one or more CPUs, on combinations of CPUs & GPUs, on single or multiple accelerator cards or modules, on a distributed processing system, or a clustered processing system. Alternatively, these or other processes may be performed by firmware running on a FPGA (Field Programmable Gate Array) architecture or one or more dedicated ASIC (Application-Specific Integrated Circuit) devices.

In some embodiments, the video processor 242 may include any video processing hardware, firmware and software components that may be configured to assemble image frames into a video stream for display and/or storage.

In some embodiments, the imaging system may include a motion processor 255. The motion processor 255 may be configured to send data and instructions to and receive data and instructions from the image generation subsystem 230, including the beamformer 232 and the ILC block 234. The motion processor 255 may be configured to send data and instructions to the image generation subsystem in order to instruct the beamformer and ILC as to which portion of an image-able region to be beamformed. The motion processor 255 may also be configured to retrieve data and instructions from the image generation subsystem 230 as needed to perform any of the various motion detection and/or motion tracking processes described herein. The motion processor may also be configured to send instructions to the TX controller 204 in order to control the transmission of tracking pings and/or imaging pings during a motion detection process and/or a motion tracking process.

The motion processor 255 may also be configured to monitor data stored in the raw data memory device 220 in order to monitor positions of fingerprints, and to retrieve raw echo data to be beamformed or otherwise processed during motion detection and/or motion tracking processes.

The motion processor 255 may also be configured to send instructions to and receive data and instructions from the video subsystem 240 so as to control images, cursors, and other elements displayed to a user, and/or to receive data from a user input device.

The motion processor may contain one or more data storage devices which may contain instructions for performing any of the various motion detection and/or motion tracking processes described herein.

Certain Terminology

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Various modifications to the above embodiments will be readily apparent to those skilled in the art, and the generic principles defined herein may be applied to other embodiments without departing from the spirit or scope of the invention. Thus, it is intended that the scope of the present invention herein disclosed should not be limited by the particular disclosed embodiments described above, but should be determined only by a fair reading of the claims that follow.

In particular, materials and manufacturing techniques may be employed as within the level of those with skill in the relevant art. Furthermore, reference to a singular item, includes the possibility that there are plural of the same items present. More specifically, as used herein and in the appended claims, the singular forms "a," "and," "said," and "the" include plural referents unless the context clearly dictates otherwise. Also as used herein, unless explicitly stated otherwise, the term "or" is inclusive of all presented alternatives, and means essentially the same as the commonly used phrase "and/or." It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs.

Certain features that are described in this disclosure in the context of separate implementations can also be implemented in combination in a single implementation. Conversely, various features that are described in the context of a single implementation can also be implemented in multiple implementations separately or in any suitable subcombination. Although features may be described above as acting in certain combinations, one or more features from a claimed combination can, in some cases, be excised from the combination, and the combination may be claimed as any subcombination or variation of any subcombination. Further, the claims may be drafted to exclude any disclosed element. As such, the foregoing sentence is intended to serve as antecedent basis for use of such exclusive terminology as "solely," "only" and the like in connection with the recitation of claim elements, or use of a "negative" limitation.

Moreover, while operations may be depicted in the drawings or described in the specification in a particular order, such operations need not be performed in the particular order shown or in sequential order, and all operations need not be performed, to achieve the desirable results. Other operations that are not depicted or described can be incorporated in the example methods and processes. For example, one or more additional operations can be performed before, after, simultaneously, or between any of the described operations. Further, the operations may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Some embodiments have been described in connection with the accompanying drawings. Some of the figures may be drawn to scale, but such scale should not be limiting, since dimensions and proportions other than what are shown are contemplated and are within the scope of the disclosed invention. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, any methods described herein may be practiced using any device suitable for performing the recited steps.

What is claimed is:

1. A method of tracking motion of an object with an imaging system comprising the steps of:
   defining a fiducial region in a region of interest with a controller of the imaging system;
   transmitting a series of unfocused ultrasound pings into the region of interest from a transducer array of the imaging system;
   receiving echoes from the series of transmitted unfocused ultrasound pings with a plurality of transducer elements of the transducer array;
   identifying a fingerprint within the fiducial region, wherein the fingerprint comprises a pattern of data in the received echoes that is identifiable as a data string;
   storing echo data received by each of the plurality of transducer elements in a separate memory string;
   detecting movement of the fingerprint with the controller; and
   communicating a signal with the controller indicating that movement of the object relative to the transducer array has occurred.

2. The method of claim 1, further comprising obtaining at least one image of the region of interest with the imaging system, and wherein defining the fiducial region comprises selecting at least one point in the at least one image.

3. The method of claim 1, wherein detecting movement of the fingerprint comprises identifying a fingerprint point in each memory string, and detecting a shift in a position of the fingerprint point in each memory string.

4. The method of claim 3, wherein the fingerprint comprises at least one machine-identifiable peak.

5. The method of claim 1, further comprising combining memory strings from two or more unfocused ultrasound pings to form a combined memory string before detecting a shift in a position of the fingerprint in the combined memory string.

6. The method of claim 1, further comprising combining memory strings from two or more transducer elements of the transducer array to form a combined memory string before detecting a shift in a position of the fingerprint in the combined memory string.

7. The method of claim 1, wherein detecting movement of the fingerprint comprises identifying a fingerprint pattern with the controller in a location other than an original location.

8. The method of claim 1, further comprising tracking motion of the object with the controller, comprising:
   obtaining a pre-movement fingerprint pattern with the controller corresponding to the fingerprint contained within the fiducial region;
   defining a search region surrounding the fingerprint with the controller;
   obtaining a plurality of post-movement search images with the controller by retrieving post-movement data corresponding to the search region surrounding the fingerprint and beamforming the search region;
   searching the search region with the controller for a new position of the pre-movement fingerprint pattern;

determining a new position for the fingerprint with the controller based on finding a fingerprint pattern in the search region; and communicating a signal with the controller indicating a new position of the fingerprint or a new position of the object.

9. The method of claim 8, wherein only the search region is beamformed and echo data that does not correspond to the search region is not beamformed during the step of tracking motion of the object.

10. The method of claim 1, further comprising detecting a shift in a position of the fingerprint based on data in a plurality of the memory strings corresponding to a plurality of receiving transducer elements.

11. The method of claim 10, wherein the plurality of receiving transducer elements are closer to opposite ends of the transducer array from one another than they are to one another.

12. The method of claim 1, wherein the fingerprint has an area of between 1 square nanometer and 100 square micrometers.

13. The method of claim 1, wherein the fiducial region lies within a free depth range defined as a range of distance from each transducer element in which returning echoes result from only a single transmitted ping, and transmitting pings at a rate greater than an inverse of a maximum round-trip travel time between a transmitting transducer element, a furthest reflector, and a receive element furthest from the transmitting element.

14. The method of claim 1, wherein the transducer array comprises a first plurality of one-dimensional linear transducer elements aligned with a first image plane and a second plurality of one-dimensional linear transducer elements aligned with a second image plane that intersects the first image plane, and wherein transmitting a series of unfocused pings into the region of interest comprises transmitting a first series of pings from a first single element of the first plurality of one-dimensional transducer elements and transmitting a second series of pings from a second single element of the second plurality of one-dimensional transducer elements.

15. The method of claim 1, wherein the transducer array comprises a first plurality of one-dimensional linear transducer elements aligned with a first image plane extending into the region of interest, a second plurality of one-dimensional linear transducer elements aligned with a second image plane extending into the region of interest, the second image plane intersecting the first image plane, and a point source transmitter element; and wherein transmitting a series of unfocused pings into the region of interest comprises transmitting a series of unfocused pings from the point source transmitter element.

16. The method of claim 15, wherein the point source transmitter element is positioned at an intersection of the first image plane and the second image plane.

* * * * *